United States Patent
Kim et al.

(10) Patent No.: US 11,432,566 B2
(45) Date of Patent: Sep. 6, 2022

(54) **FEED COMPOSITION FOR PREVENTING OR TREATING ACUTE HEPATOPANCREATIC NECROSIS DISEASE (AHPND) OR WHITE SPOT SYNDROME (WSS), COMPRISING A *BACILLUS SUBTILIS* STRAIN, A *BACILLUS PUMILUS* STRAIN, AND A *BACILLUS LICHENIFORMIS* STRAIN AS ACTIVE INGREDIENTS**

(71) Applicant: CJ Cheiljedang Corporation, Seoul (KR)

(72) Inventors: Ji Eun Kim, Gyeonggi-do (KR); Sung Hun Kim, Gyeonggi-do (KR); Jae Won Kim, Gyeonggi-do (KR); Seo Hyung Woo, Gyeonggi-do (KR); Jongsu Eun, Gyeonggi-do (KR); Hayun Jo, Gyeonggi-do (KR); Jee Eun Han, Daegu (KR)

(73) Assignee: CJ CHEILDEJANG CORPORATION, Seoul (KR)

( * ) Notice: Subject to any disclaimer, the term of this patent is extended or adjusted under 35 U.S.C. 154(b) by 0 days.

(21) Appl. No.: 16/349,838

(22) PCT Filed: Dec. 28, 2018

(86) PCT No.: PCT/KR2018/016883
§ 371 (c)(1),
(2) Date: May 14, 2019

(87) PCT Pub. No.: WO2019/132600
PCT Pub. Date: Jul. 4, 2019

(65) Prior Publication Data
US 2020/0315210 A1    Oct. 8, 2020

(30) Foreign Application Priority Data

Dec. 29, 2017  (KR) .................. 10-2017-0184265
Dec. 27, 2018  (KR) .................. 10-2018-0171280

(51) Int. Cl.
| | |
|---|---|
| A61K 39/07 | (2006.01) |
| A61K 39/02 | (2006.01) |
| A61K 35/742 | (2015.01) |
| A23K 50/80 | (2016.01) |
| A23K 10/18 | (2016.01) |
| A61P 1/18 | (2006.01) |
| A61K 35/741 | (2015.01) |

(52) U.S. Cl.
CPC .............. *A23K 10/18* (2016.05); *A23K 50/80* (2016.05); *A61K 35/741* (2013.01); *A61K 35/742* (2013.01); *A61K 39/07* (2013.01); *A61K 39/107* (2013.01); *A61P 1/18* (2018.01)

(58) Field of Classification Search
None
See application file for complete search history.

(56) References Cited

U.S. PATENT DOCUMENTS

2015/0216915 A1   8/2015   Frouel et al.
2016/0128337 A1   5/2016   Carpenter et al.

FOREIGN PATENT DOCUMENTS

| CN | 103403146 A | 11/2013 |
|---|---|---|
| CN | 104195068 A | 12/2014 |
| CN | 103301409 B | 1/2015 |
| JP | 2015517807 A | 6/2015 |
| KR | 1020070115017 A | 12/2007 |
| KR | 1020080061582 A | 7/2008 |
| KR | 100977407 | 8/2010 |
| KR | 102011035554 | 4/2011 |
| KR | 1020120088436 A | 8/2012 |
| KR | 101242821 B1 | 3/2013 |
| KR | 101370943 B1 | 3/2013 |
| KR | 1020130047329 A | 5/2013 |
| KR | 101230813 B1 | 6/2013 |
| KR | 1020160096876 A | 8/2016 |
| WO | 2012/105804 A2 | 8/2012 |
| WO | 2012105804 A2 | 8/2012 |
| WO | 2012105805 A2 | 8/2012 |
| WO | 2013/155468 A2 | 10/2013 |
| WO | 2013151364 A1 | 10/2013 |
| WO | 2013155468 A2 | 10/2013 |
| WO | 2016073981 A1 | 5/2016 |
| WO | 2017031371 A1 | 2/2017 |
| WO | 2017/147130 A2 | 8/2017 |
| WO | 2017147130 A2 | 8/2017 |

OTHER PUBLICATIONS

Machine translation of KR 101 370 943 B1, pp. 1-10, 2014.*
Verma, Arunima Kumar et al., "An Update on Mechanism of Entry of White Spot Syndrome Virus into Shrimps", Fish & Shellfish Immunology, Electronic publication on Jun. 3, 2017, vol. 67, pp. 141-146.
Li, Peng et al., "Acute Hepatopancreatic Necrosis Disease-causing Vibrio Parahaemolyticus Strains Maintain an Antibacterial Type VI Secretion System with Versatile Effector Repertoires", Applied and Environmental Microbiology, Jul. 2017, vol. 83. No. 13. document No. e00737-17, pp. 1-17.
International Search Report, PCT/KR2018/016883 Prepared by the Korean Patent Office, dated Apr. 5, 2019, 9 pages including English Translation.

(Continued)

*Primary Examiner* — Sarvamangala Devi
(74) *Attorney, Agent, or Firm* — Brooks Kushman P.C.

(57) ABSTRACT

A feed composition for preventing or treating acute hepatopancreatic necrosis disease (AHPND) or white spot syndrome (WSS), having a *Bacillus subtilis* (KCCM11143P) strain, a *Bacillus pumilus* (KCCM11144P) strain, and a *Bacillus licheniformis* (KCCM11270P) strain; culture media thereof; concentrates thereof; or dry matters thereof as an active ingredient. The feed composition exhibits antibacterial activity against *Vibrio parahaemolyticus*, which causes shrimp AHPND, and antiviral activity against white spot syndrome virus (WSSV), which causes WSS.

10 Claims, 6 Drawing Sheets

(56) References Cited

OTHER PUBLICATIONS

Liu; Isolation and characterisation of *Bacillus* spp. antagonistic to *Vibrio parahaemolyticus* for use as probiotics in aquaculture, World J. Microbiol Biotechnol, pp. 77-803, 2005.

Vinoj; Inhibitory effects of *Bacillus licheniformis*(DAB1) and *Pseudomonas aeruginosa*(DAP1) against *Bivrio parahaemolyticus* isolated from Fenneropenaeus indicus, Aquacult Int vol. 21, pp. 1121-1135, 2013.

Chai; Dietary supplementation of probiotic*Bacillus* PC465 isolated from the gut of Fenneropenaeus chinensisimproves the health status and resistance of Litopenaeus vannameiagainst white spot syndrome virus, Fish & Shellfish Immunology, Fish & Shellfish Immunology 54 (2016) 602-611, vol. 54, pp. 602-611, 2016.

Li, Dietary probiotic *Bacillus* OJ and isomaltooligosaccharides influence the intestine microbial populations, immune responses and resistance to white spot syndrome birus in shrimp(*Litopenaeus vannamei*), Aquaculture, vol. 291, pp. 35-40, 2009.

Sanchez-Ortiz; Effect of mixed-*Bacillus* spp isolated from pustulose arkAnadara tuberculosaon growth, survival, viral prevalence and immune-related gene expression in shrimp*Litopenaeus vannamei*, Fish & Shellfish Immunology, vol. 59, pp. 95-102, 2016.

Supplementary European Search Report EP18859986, dated Sep. 22, 2020.

Lavens, Partrick, Probiotics and Health Boosters Reduce Mortality and Pathology in a Standardized AHPND Challenge Model, Latin American & Caribbean Aquaculture, abstract, Nov. 7, 2017.

Anonymous, New and enhanced formulation for Sanolife PRO-2 probiotic, www.INVEAquaculture.com, Aug. 1, 2017.

Supplemental European Search Report, EP App. No. 18859986, dated May 11, 2020.

Loc Tran et al., Determination of the infectious nature of the agent of acute hepatopancreatic necrosis syndrome affecting penaeid shrimp, Diseases of Aquatic Organisms Dis Aquat Org, vol. 105: 45-55, 2013, doi: 10.3354/dao02621, Published Jul. 9, 2013.

OANH Dang Thi Hoang et. al.; Probiotics benefit Pacific white shrimp challenged with AHPND, Responsible Seafood Advocate, www.globalseafood.org, May 26, 2016.

Anyanomous; New and enhanced formulation for Sanolife Pro-2 probiotic, INVE Aquaculture, www.inveaquaculture.com/latest-news, Aug. 1, 2017.

Song Xiaoling et al.; The effect of adding *Bacillus* to feed on the antiviral infectivity and disease resistance gene expression of Litopenaeus vannamei, The 2013 Symposium of the Fish Disease, p. 289, dated Nov. 5, 2013.

* cited by examiner

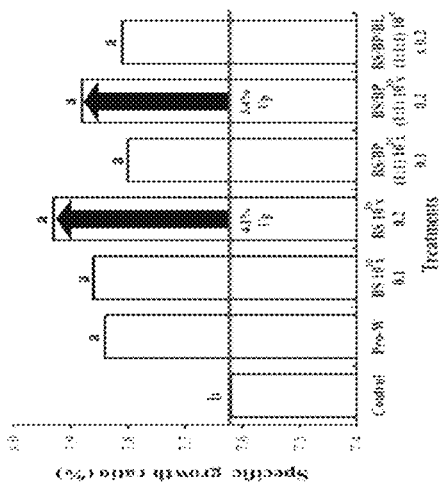
Fig. 4A
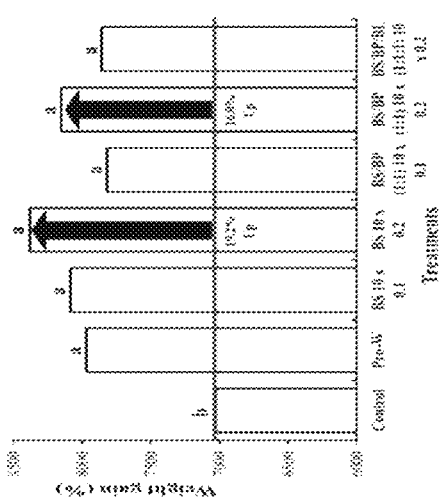
Fig. 4B
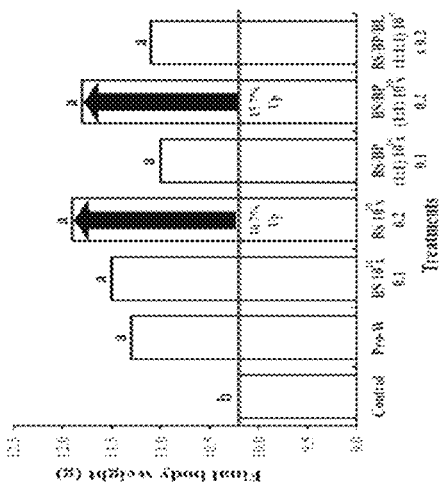
Fig. 4C
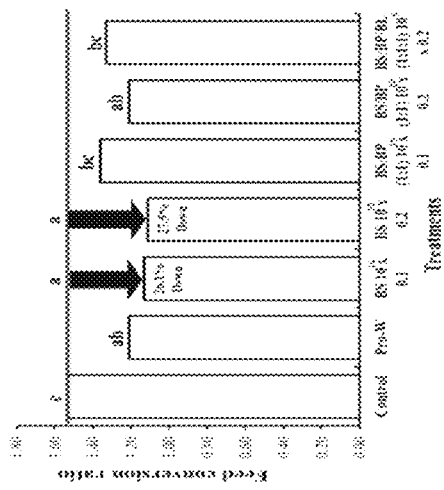
Fig. 4D
Fig. 4E

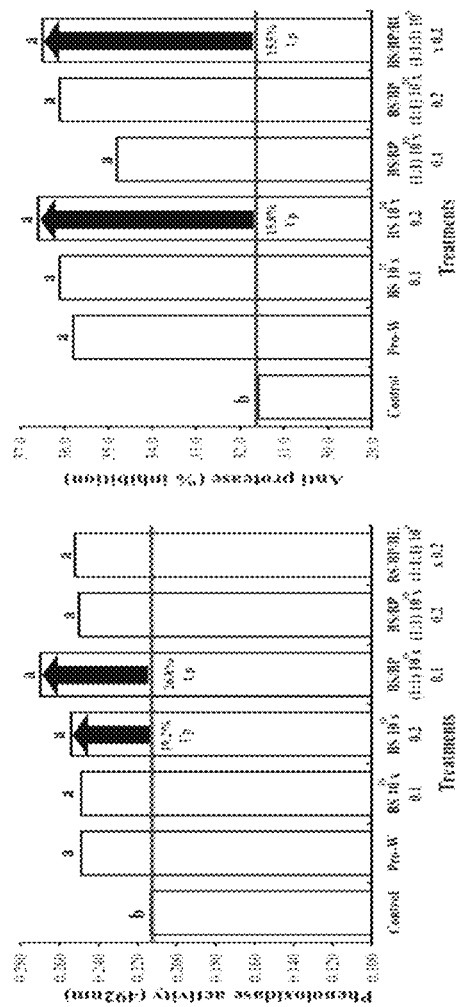
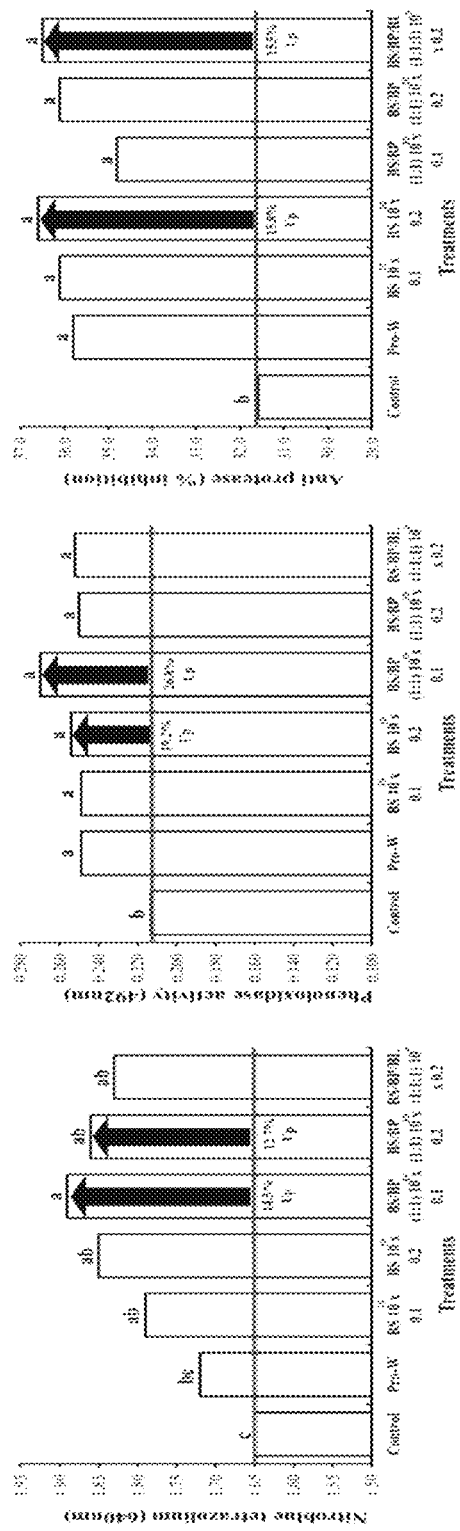
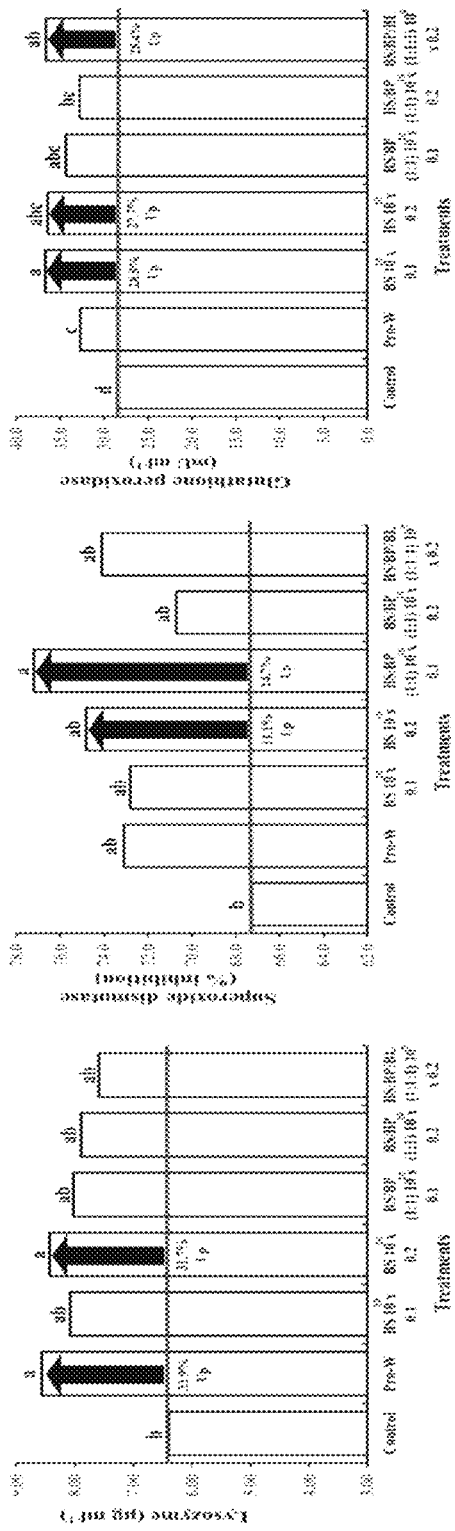
Fig. 5A  Fig. 5B  Fig. 5C
Fig. 5D  Fig. 5E  Fig. 5F

FEED COMPOSITION FOR PREVENTING OR TREATING ACUTE HEPATOPANCREATIC NECROSIS DISEASE (AHPND) OR WHITE SPOT SYNDROME (WSS), COMPRISING A *BACILLUS SUBTILIS* STRAIN, A *BACILLUS PUMILUS* STRAIN, AND A *BACILLUS LICHENIFORMIS* STRAIN AS ACTIVE INGREDIENTS

CROSS-REFERENCE TO RELATED APPLICATION

This application is the U.S. national phase of PCT Application No. PCT/KR2018/016883 filed on Dec. 28, 2018, which claims priority to KR Patent Application No. 10-2017-0184265 filed on Dec. 29, 2017, and KR Patent Application No. 10-2018-0171280 filed on Dec. 27, 2018, the disclosures of which are incorporated in their entirety by reference herein.

A feed composition for preventing or treating acute hepatopancreatic necrosis disease (AHPND) or white spot syndrome (WSS), comprising a *Bacillus subtilis* strain, a *Bacillus pumilus* strain, and a *Bacillus licheniformis* strain as active ingredients

TECHNICAL FIELD

The present disclosure relates to a feed composition for preventing or treating acute hepatopancreatic necrosis disease (AHPND) or white spot syndrome (WSS), comprising a *Bacillus subtilis* strain, a *Bacillus pumilus* strain, and a *Bacillus licheniformis* strain; culture media thereof; concentrates thereof; or dry matters thereof as an active ingredient.

BACKGROUND ART

Early mortality syndrome (EMS), acute hepatopancreatic necrosis disease (AHPND), and acute hepatopancreatic necrosis syndrome (AHPNS) are rapidly growing diseases in shrimp farming, and *Vibrio parahaemolyticus* is an etiologic agent of these diseases; that is, *Vibrio parahaemolyticus* produces insect toxins causing 100% lethality within 6 hours or within a week (Tran et al. 2013. Dis aquat Org 105:45-55). Insect toxins are produced by the expression of specific genes present in a specific plasmid of the bacteria (i.e., *photorhabdus* insect-related toxins; Pir toxin), and are easily moved around, that is, they have motility. In this regard, these diseases spread more rapidly than viral shrimp diseases such as white spot syndrome virus (WSSV), Taura syndrome virus (TSV), infectious myonecrosis virus (IMNV), etc., which have recently received attention. AHPND began in China in 2009, and spread rapidly in Asian counties (e.g., Thailand, Malaysia, and Vietnam) within one year, and further occurred in Mexico to spread to other Central American countries, resulting in damage to most of the shrimp markets. South Korea also suffered great damage due to AHPND from 2015 to 2016, and studies are currently underway to prevent or manage the disease.

Recently, due to demand from consumers for safe products and the production strategy for continuous farming, therapeutic agents used to treat existing pathogenic bacteria are restricted by farming-related regulations. Therefore, in shrimp farming, it is necessary to take into consideration not only the quality and breeding method of seed goods, but also important factors controlling diseases.

Meanwhile, probiotics are defined as microbial preparations or components that assist the balance of microorganisms in the intestine, and have an etymological meaning that is opposite to antibiotics, which refers to an antibiotic material. Representatively, examples of the probiotics include lactic acid bacteria such as *Lactobacillus* and *Bifidobacterium*. Additionally, probiotics do not possess toxic genes against humans and animals, nor do they produce pathogenic substances, and thus are classified as GRAS (generally recognized as safe). Therefore, development of a feed additive using probiotics, the safety of which is demonstrated, has been actively accomplished.

As an example, Korean Patent Publication No. 10-2011-035554 discloses a mixed strain of novel CMB L1 of the genus *Bacillus* and CMB201 of the genus *Lactobacillus*, a food composition for anticancer and immunity enhancement using the same, and a microbial preparation having antibacterial activity. In addition, Korean Patent No. 10-0977407 discloses an immune booster and feed additive for animals, containing lysates of *Zygosaccharomyces bailii*, which increase the various activities of neutrophils, the major phagocytic cells of animals, and enhances non-specific defense against attack inoculation by pathogenic bacteria. However, the actual immunoactivity of the feed additive using probiotics is inadequate, and thus research on a feed additive using probiotics still having excellent immunoactivity is needed.

DISCLOSURE

Technical Problem

The present inventors have made intensive efforts to develop a shrimp feed supplemented with probiotics (*Bacillus* sp.) for preventing shrimp AHPND or white spot syndrome (WSS). As a result, they have confirmed that when the feed composition supplemented with *Bacillus subtilis*, *Bacillus pumilus*, and *Bacillus licheniformis* is fed to a shrimp, the survival rate of a shrimp against AHPND infection (caused by a strain isolated from the affected area in Vietnam in 2013; Tran et. al. 2013.) or WSSV infection is improved, and that the growth rate and non-specific immunity of shrimp are not only increased but also the water quality is improved and the production of high-protein shrimp can be produced, thereby completing the present disclosure.

Technical Solution

An object of the present disclosure is to provide a feed composition for preventing or treating acute hepatopancreatic necrosis disease (AHPND), comprising a *Bacillus subtilis* strain, a *Bacillus pumilus* strain, and a *Bacillus licheniformis* strain; culture media thereof; concentrates thereof; or dry matters thereof as an active ingredient.

Another object of the present disclosure is to provide a method for preventing or treating acute hepatopancreatic necrosis disease, comprising administering the feed composition to a subject.

Still another object of the present disclosure is to provide a feed composition for preventing or treating white spot syndrome (WSS), comprising a *Bacillus subtilis* strain, a *Bacillus pumilus* strain, and a *Bacillus licheniformis* strain; culture media thereof; concentrates thereof; or dry matters thereof as an active ingredient.

Still another object of the present disclosure is to provide a method for preventing or treating white spot syndrome, comprising administering the feed composition to a subject.

Advantageous Effects

The composition of the present disclosure, which comprises a *Bacillus subtilis* (KCCM11143P) strain, a *Bacillus pumilus* (KCCM11144P) strain, and a *Bacillus licheniformis* (KCCM11270P) strain as active ingredient, has antibacterial activity against *Vibrio parahaemolyticus*, which causes AHPND which is problematic in shrimp farming, and antiviral activity against white spot syndrome virus, which causes WSS, and exhibits an effect of improving immunity of the shrimp hepatopancreas, and thus the composition of the present disclosure can be used as a shrimp feed composition or a feed additive.

BRIEF DESCRIPTION OF DRAWINGS

FIG. 4 is graphs showing the growth rates of shrimp. FIGS. 4(a) to 4(d) show the final body weight, the weight gain rate, the daily growth rate, and the feed conversion rate, respectively.

FIG. 5 is graphs analyzing the non-specific immunities of shrimp. FIGS. 5(a) to 5(e) show the activities against macrophages, phenoloxidase, antiproteinase, lysozyme, and superoxide dismutase, respectively.

BEST MODE FOR CARRYING OUT THE INVENTION

Figure 1:
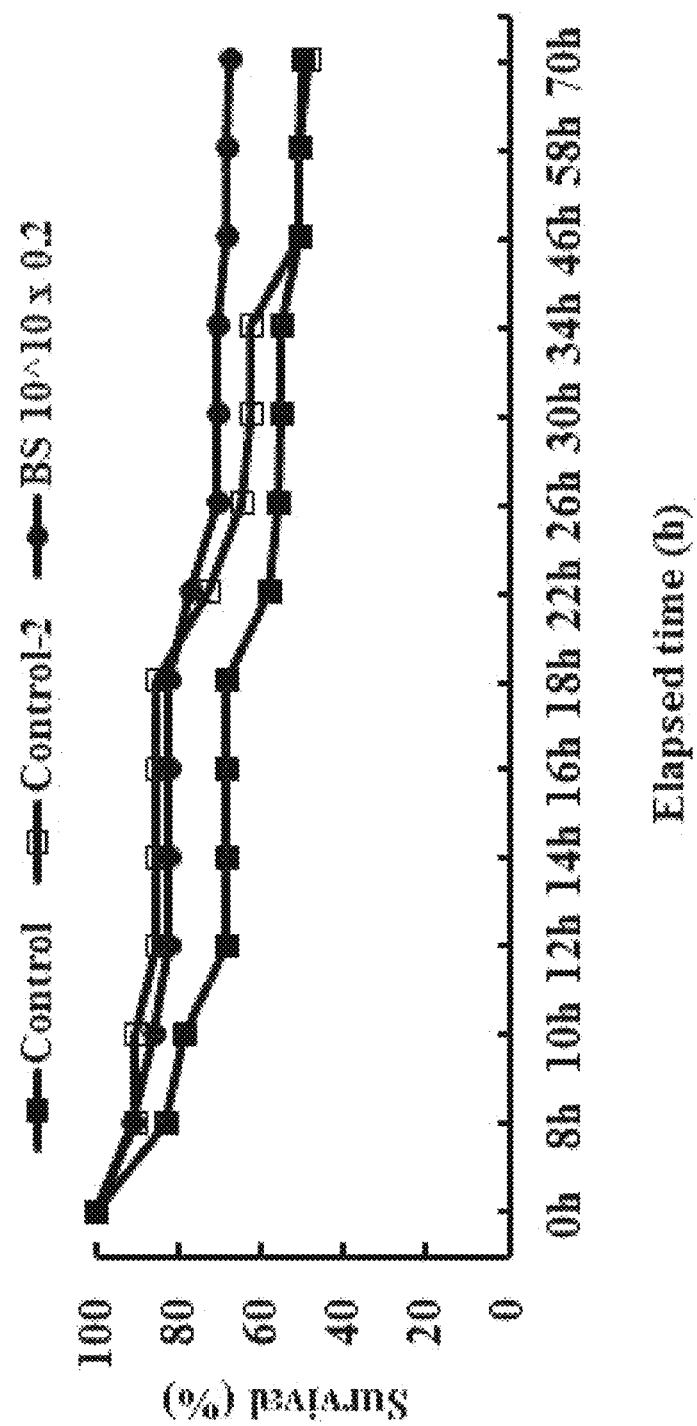
FIG. 1 is a graph showing the survival rate of shrimp infected with *Vibrio parahaemolyticus*.

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the above objects, an aspect of the present disclosure provides a feed composition for preventing or treating acute hepatopancreatic necrosis disease (AHPND), comprising a *Bacillus subtilis* strain, a *Bacillus pumilus* strain, and a *Bacillus licheniformis* strain; culture media thereof; concentrates thereof; or dry matters thereof as an active ingredient.

As used herein, the term "*Bacillus subtilis*" is an aerobic bacterium that is not toxic and produces spores. *Bacillus subtilis* is widely distributed in nature such as in dry grass, soil, sewage, air, etc. This bacterium is widely used in industry because it produces enzymes to coagulate milk, saccharifies starch, and decomposes fat and oil. The optimal conditions for growth of the bacterium are a pH of 7 to 8.5 and a temperature of 37° C. to 40° C. Due to the characteristics of a strain of the genus *Bacillus*, the strain does not possess toxic genes for humans and animals, is non-pathogenic, produces no pathogenic substances, and exhibits a rapid growth rate in vivo. *Bacillus subtilis* has an anaerobic habitat in the presence of glucose, etc., and endospores allow *Bacillus* to survive in extremely harsh environments such as high or low temperatures.

As used herein, the term "*Bacillus pumilus*" is an aerobic gram-positive bacterium producing spores. *Bacillus pumilus* is distributed in the form of colonies in soil or present in the roots of some plants. *Bacillus pumilus* spores are generally highly resistant to environmental stresses including exposure to ultraviolet rays, desiccation, and the presence of oxidizing agents such as hydrogen peroxide.

As used herein, the term "*Bacillus licheniformis*" is a bacterium commonly found in soil, and is a mesophilic gram-positive bacterium. The optimal growth temperature of this bacterium is about 50° C., but it can survive even at much higher temperatures. *Bacillus licheniformis* may exist in the form of dormant spores to resist harsh environments.

In the present disclosure, the *Bacillus subtilis* may be a strain deposited with Accession No. KCCM11143P.

In the present disclosure, the *Bacillus pumilus* may be a strain deposited with Accession No. KCCM11144P.

In the present disclosure, the *Bacillus licheniformis* may be a strain deposited with Accession No. KCCM11270P.

In the present disclosure, a feed composition comprising the *Bacillus subtilis* (KCCM11143P), the *Bacillus pumilus* (KCCM11144P), and the *Bacillus licheniformis* (KCCM11270P) was prepared.

The composition of the present disclosure may comprise the *Bacillus subtilis* (KCCM11143P), the *Bacillus pumilus* (KCCM11144P), and the *Bacillus licheniformis* (KCCM11270P), which have a bacterial count of $1 \times 10^4$ CFU to $1 \times 10^{11}$ CFU per gram of the total active ingredients. Specifically, the bacterial count may be $1 \times 10^4$ CFU/g to $1 \times 10^{10}$ CFU/g, and more specifically, the composition of the present disclosure comprises the *Bacillus subtilis* (KCCM11143P), *Bacillus pumilus* (KCCM11144P), and *Bacillus licheniformis* (KCCM11270P), which have the bacterial count of $1 \times 10^8$ CFU/g to $1 \times 10^{10}$ CFU/g.

For the objects of the present disclosure, *Bacillus subtilis* contained in the feed composition as an active ingredient may only comprises *Bacillus subtilis* (KCCM11143P).

For the objects of the present disclosure, *Bacillus pumilus* contained in the feed composition as an active ingredient may comprise only *Bacillus pumilus* (KCCM11144P).

For the objects of the present disclosure, *Bacillus licheniformis* contained in the feed composition as an active ingredient may comprise only *Bacillus licheniformis* (KCCM11270P).

As used herein, the term "acute hepatopancreatic necrosis disease (AHPND)" refers to a disease named early mortality syndrome (EMS) or acute hepatopancreatic necrosis syndrome (AHPNS), and collectively refers to mass mortality caused by pathogens within 30 days of standing in an aquafarm. AHPND is caused by *Vibrio parahaemolyticus*, a pathogenic bacterium present in seawater, which has a large number of infections in whiteleg shrimp, accounting for about 96% of Korean farmed shrimp. Because of a high mortality rate in the early stages of life, it causes harm to shrimp, but it is harmless to humans. The *Vibrio parahaemolyticus* is a gram-negative *bacillus* belonging to the genus *Vibrio*, which causes acute food poisoning and enteritis in humans and causes vibriosis in fish. Recently, *Vibrio parahaemolyticus* has been identified as a causative bacterium of acute hepatopancreatic necrosis disease (AHPND), which causes mass mortality in the shrimp farming industry.

As used herein, the term "prevention" refers to any behavior resulting in suppression or delay of symptoms of shrimp AHPND by administering the composition according to the present disclosure, which comprises *Bacillus subtilis*.

As used herein, the term "treatment" refers to any action resulting in alleviation of or full recovery from symptoms of shrimp AHPND by administering the composition according to the present disclosure, which comprises *Bacillus subtilis* (KCCM11143P).

In addition to the above strains contained as active ingredients, the composition may include a known carrier or an additive which is acceptable for pharmaceutical, food, or feed use. In the present disclosure, as a probiotic preparation having antibacterial activity against *Vibrio parahaemolyticus*, which comprises the *Bacillus subtilis* (KCCM11143P), *Bacillus pumilus* (KCCM11144P), and *Bacillus licheniformis* (KCCM11270P), there may be a binder, an emulsifier, a preservative, and the like, which are added in order to prevent deterioration of the quality of the probiotic preparation; and there may be an amino acid, a vitamin, an enzyme, a flavoring agent, a non-protein nitrogen compound, a silicate, a buffering agent, an extractant, an oligosaccharide, and the like, which are added to a feed to increase the efficiency of the probiotic preparation. In addition, a feed mixture, etc. may be further comprised, but the present disclosure is not limited thereto.

In an embodiment of the present disclosure, as a result of confirming whether feeding the feed composition to shrimp would increase the immunity against AHPND and exhibit the disease preventive effect, it was confirmed that the groups (BS+BP+BL Groups 1 and 2), in which the feed compositions (Examples 5 and 6) including the *Bacillus subtilis* (KCCM11143P) strain, *Bacillus pumilus* (KCCM11144P) strain, and *Bacillus licheniformis* (KCCM11270P) strain of the present disclosure are administered, could increase the disease resistance of shrimp against infection of *Vibrio parahaemolyticus* and significantly lower the toxin amount of AHPND in the shrimp hepatopancreas, compared to the groups (BS Groups 3 and 4), in which Comparative Example 1 (not including probiotics), and Comparative Examples 3 and 4 (including only *Bacillus subtilis*) are administered.

In other embodiment of the present disclosure, as a result of analyzing the non-specific immunity of the feed composition including the strains above, it was found that the macrophage (NBT) activity, glutathione peroxidase (GPx) activity, lysozyme activity, phenol oxidase (PO) activity, superoxide dismutase (SOD) activity, and antiprotease activity were remarkably higher than those of the Comparative Examples. Based on this result, it can be seen that the composition may be useful for increasing the non-specific immune response of shrimp or improving the immunity thereof.

The present disclosure provides a feed additive for shrimp farming, comprising the above-mentioned feed composition.

In the feed additive of the present disclosure, a known carrier or a stabilizer which is acceptable for pharmaceutical, food, or feed use may be added in addition to the above active ingredients. When necessary, all sorts of nutrients such as vitamins, amino acids, and minerals, antioxidants, and other additives may be added, whose shape may be convenient therefor, such as powder, granules, pellets, and suspensions. When supplying the feed additive according to the present disclosure, the feed additive may be supplied alone or mixed with feed to non-ruminant animals.

Additionally, the present disclosure provides a feed for shrimp farming, comprising the above-mentioned feed additive.

The *Bacillus subtilis* (KCCM11143P) strain, *Bacillus pumilus* (KCCM1114P) strain, and *Bacillus licheniformis* (KCCM11270P) strain of the present disclosure, which are gram-positive bacteria having a sporulation capacity, are preferably formulated in a spore form, but are not limited thereto. The feed of the present disclosure is not particularly limited, but any feed such as powder feed, solid feed, moist pellet feed, dry pellet feed, extruder pellet (EP) feed, and raw feed is available.

As described above, the *Bacillus* sp. forms endogenous spores, and thus is very stable against heat. Therefore, the *Bacillus subtilis* (KCCM11143P), *Bacillus pumilus* (KCCM1114P), and *Bacillus licheniformis* (KCCM11270P) of the present disclosure can be prepared separately as a feed additive form and then mixed with a feed, or can be prepared by directly adding to a feed when preparing the feed. The *Bacillus subtilis*, *Bacillus pumilus*, and *Bacillus licheniformis* included in the feed of the present disclosure may be in a liquid or dry state, and preferably in the form of a dried powder. The drying process may be performed by air drying, natural drying, spray drying, and freeze-drying, but is not limited thereto. The *Bacillus subtilis* (KCCM11143P), *Bacillus pumilus* (KCCM1114P), and *Bacillus licheniformis* (KCCM11270P) of the present disclosure may be mixed as a powder form in an amount of 0.05% to 10% by weight, preferably 0.1% to 1% by weight, based on the weight of the feed. The *Bacillus subtilis*, *Bacillus pumilus*, and *Bacillus licheniformis* of the present disclosure may be mixed at a concentration ratio of 1 to 5:1 to 5:1 to 5. In addition, the feed is used for aquaculture, and in addition to the *Bacillus subtilis* (KCCM11143P), *Bacillus pumilus* (KCCM1114P), and *Bacillus licheniformis* (KCCM11270P) of the present disclosure, it may further include conventional additives capable of increasing the preservability of the feed.

In order to achieve the above objects, another aspect of the present disclosure provides a method for preventing or treating acute hepatopancreatic necrosis disease, comprising administering the feed composition of the present disclosure to a subject.

Herein, the acute hepatopancreatic necrosis disease, prevention, and treatment of the present disclosure are as described above.

As used herein, the term "subject" may refer to fish or crustaceans, the farming of which is possible, and which have or are at risk of developing acute hepatopancreatic necrosis disease, but the subject may refer to shrimp according to the objects of the present disclosure.

The feed is preferably supplied with the same amount and at the same feeding interval as conventional feeds. In addition, the pathogenic bacterium refers to a bacterium that causes, in shrimp farming, mass mortality of shrimp by inducing AHPND, and specifically may refer to *Vibrio parahaemolyticus*.

Causes of mass mortality in the shrimp farming include not only the *Vibrio parahaemolyticus* but also the infection by various viruses and the concentration of ammonia in breeding water. In the shrimp farming, ammonia in breeding water occurs as a metabolite of proteins such as shrimp feces, feed waste, etc., and it varies greatly with the increase of pH and water temperature. Ammonia at a high concentration is a direct cause of acute death of shrimp, leading to mass mortality; and ammonia at a low concentration may lead to a reduction in the growth as well as feeding capacity and immunity of shrimp in the long term, which in turn can lead to the development of various diseases.

In an embodiment of the present disclosure, the breeding water of shrimp in which the feed composition of the present disclosure had been fed was collected and analyzed, and as a result, it was found that the total ammonia concentration in the breeding water was significantly lower than that of the control, and thereby the *Bacillus subtilis* (KCCM11143P) strain, *Bacillus pumilus* (KCCM11144P) strain, and *Bacillus*

*licheniformis* (KCCM11270P) strain of the present disclosure could improve water quality of the shrimp-breeding water.

As described above, the *Bacillus subtilis* (KCCM11143P), *Bacillus pumilus* (KCCM1114P), and *Bacillus licheniformis* (KCCM11270P) of the present disclosure can not only enhance the disease resistance of shrimp, but can also inhibit the toxin of AHPND in the shrimp hepatopancreas. Therefore, by using the strains, the effect of preventing *Vibrio parahaemolyticus* that causes the disease can be obtained and the effect of enhancing the resistance to white spot syndrome virus also can be obtained, and thereby shrimp can be farmed more safely.

In order to achieve the above objects, still another aspect of the present disclosure provides a feed composition for preventing or treating white spot syndrome (WSS), comprising a *Bacillus subtilis* strain, a *Bacillus pumilus* strain, and a *Bacillus licheniformis* strain; culture media thereof; concentrates thereof; or dry matters thereof as an active ingredient.

The terms of the present disclosure *Bacillus subtilis, Bacillus pumilus, Bacillus licheniformis*, prevention, and treatment are as described above.

The composition of the present disclosure may comprise the *Bacillus subtilis* (KCCM11143P), the *Bacillus pumilus* (KCCM11144P), and the *Bacillus licheniformis* (KCCM11270P), which have a bacterial count of $1 \times 10^4$ CFU to $1 \times 10^{11}$ CFU per gram of the total active ingredients. Specifically, the bacterial count may be $1 \times 10^4$ CFU/g to $1 \times 10^{10}$ CFU/g, and more specifically, the composition of the present disclosure comprises the *Bacillus subtilis* (KCCM11143P), *Bacillus pumilus* (KCCM11144P), and *Bacillus licheniformis* (KCCM11270P), which have the bacterial count of $1 \times 10^8$ CFU/g to $1 \times 10^{10}$ CFU/g.

As used herein, the term "white spot syndrome virus (WSSV)" refers to a virus widely distributed all over the world. Because WSSV has a tail-like attachment at the end of a virion, and possesses a form similar to an egg-shaped *bacillus* in which a rod-shaped capsid and an envelope are present, it was referred to as baculovirus or *bacillus*-like formed virus; however, recently, it has been renamed whispovirus, which is a genetically new viral group. The virus has a length of about 275 nm and a diameter of about 120 nm, and is composed of double-stranded DNA having a size of about 290 kb.

The composition may include, in addition to the above strains contained as active ingredients, a known carrier or an additive which is acceptable for pharmaceutical, food, or feed use. In the present disclosure, as a probiotic preparation having antiviral activity against white spot syndrome virus, which comprises the *Bacillus subtilis* (KCCM11143P), *Bacillus pumilus* (KCCM11144P), and *Bacillus licheniformis* (KCCM11270P), there may be a binder, an emulsifier, a preservative, and the like, which are added in order to prevent deterioration of the quality of the probiotic preparation; and there may be an amino acid, a vitamin, an enzyme, a flavoring agent, a non-protein nitrogen compound, a silicate, a buffering agent, an extractant, an oligosaccharide, and the like, which are added to a feed to increase the efficiency of the probiotic preparation. In addition, a feed mixture, etc. may be further comprised, but the present disclosure is not limited thereto.

In an embodiment of the present disclosure, as a result of confirming whether feeding the feed composition to shrimp would increase the immunity against white spot syndrome and exhibit the disease preventive effect, it was confirmed that the groups (BS+BP+BL Groups 1 and 2), in which the feed compositions (Examples 5 and 6) including the *Bacillus subtilis* (KCCM11143P) strain, *Bacillus pumilus* (KCCM11144P) strain, and *Bacillus licheniformis* (KCCM11270P) strain of the present disclosure are administered, could increase the disease resistance of shrimp against infection of white spot syndrome virus (WSSV), compared to the group (BS Group 4), in which Comparative Example 1 (not including probiotics) and the feed composition (Comparative Example 4) including only the *Bacillus subtilis* KCCM11143P strain are administered.

In other embodiment of the present disclosure, as a result of confirming whether the resistance to complex infection of the white spot syndrome virus (WSSV) and acute hepatopancreatic necrosis disease (AHPND) would be increased, and whether the survival rate-enhancing effect would be exhibited when the feed composition is fed to shrimp, it was confirmed that the groups (BS+BP+BL Groups 1 and 2), in which the feed compositions (Examples 5 and 6) including the *Bacillus subtilis* (KCCM11143P) strain, *Bacillus pumilus* (KCCM11144P) strain, and *Bacillus licheniformis* (KCCM11270P) strain are administered, could enhance the disease resistance of shrimp against the complex infection of the WSSV and AHPND, compared to the group (BS Group 4), in which Comparative Example 1 (not including probiotics) and the feed composition (Comparative Example 4) including only the *Bacillus subtilis* (KCCM11143P) strain are administered.

The present disclosure provides a feed additive for shrimp farming, comprising the above-mentioned feed composition.

In the feed additive of the present disclosure, a known carrier or a stabilizer which is acceptable for pharmaceutical, food, or feed use may be added in addition to the above active ingredients. When necessary, all sorts of nutrients such as vitamins, amino acids, and minerals, antioxidants, and other additives may be added, whose shape may be convenient therefor, such as powder, granules, pellets, and suspensions. When supplying the feed additive according to the present disclosure, the feed additive may be supplied alone or mixed with feed to non-ruminant animals.

Additionally, the present disclosure provides a feed for shrimp farming, comprising the above-mentioned feed additive.

The *Bacillus subtilis* (KCCM11143P) strain, *Bacillus pumilus* (KCCM1114P) strain, and *Bacillus licheniformis* (KCCM11270P) strain of the present disclosure, which are gram-positive bacteria having a sporulation capacity, are preferably formulated in a spore form, but are not limited thereto. The feed of the present disclosure is not particularly limited, but any feed such as powder feed, solid feed, moist pellet feed, dry pellet feed, extruder pellet (EP) feed, and raw feed is available.

As described above, the *Bacillus* sp. forms endogenous spores, and thus is very stable against heat. Therefore, the *Bacillus subtilis* (KCCM11143P), *Bacillus pumilus* (KCCM1114P), and *Bacillus licheniformis* (KCCM11270P) of the present disclosure can be prepared separately as a feed additive form and then mixed with a feed, or can be prepared by directly adding to a feed when preparing the feed. The *Bacillus subtilis, Bacillus pumilus,* and *Bacillus licheniformis* included in the feed of the present disclosure may be in a liquid or dry state, and preferably in the form of a dried powder. The drying process may be performed by air drying, natural drying, spray drying, and freeze-drying, but is not limited thereto. The *Bacillus subtilis* (KCCM11143P), *Bacillus pumilus* (KCCM1114P), and *Bacillus licheniformis* (KCCM11270P) of the present disclosure may be mixed as a powder form in an amount of 0.05% to 10% by weight, preferably 0.1% to 1% by weight, based on the weight of the feed. In addition, the feed is used for aquaculture, and may further include, in addition to the *Bacillus subtilis* (KCCM11143P), *Bacillus pumilus* (KCCM1114P), and *Bacillus licheniformis* (KCCM11270P) of the present disclosure, conventional additives capable of increasing the preservability of the feed.

In order to achieve the above objects, still another aspect of the present disclosure provides a method for preventing or treating white spot syndrome, comprising administering the feed composition of the present disclosure to a subject.

Herein, the terms of the present disclosure, the white spot syndrome, prevention, treatment, and subject are as described above.

Causes of mass mortality in the shrimp farming include not only the *Vibrio parahaemolyticus* but also the infection by various viruses. Specifically, the virus may refer to white spot syndrome virus (WSSV).

As described above, the *Bacillus subtilis* (KCCM11143P), *Bacillus pumilus* (KCCM1114P), and *Bacillus licheniformis* (KCCM11270P) of the present disclosure can obtain an effect of enhancing the resistance to white spot syndrome virus (WSSV), and thus shrimp can be farmed more safely.

MODE FOR CARRYING OUT THE INVENTION

Hereinafter, the present disclosure will be described in detail through exemplary embodiments. However, these exemplary embodiments are for illustrative purposes only and are not intended to limit the scope of the present disclosure.

Preparation Example 1. Selection of Probiotics with Antibacterial Activity

To select strains having antibacterial activity against *Vibrio parahaemolyticus*, which induces shrimp AHPND, a clear zone assay was performed. 0.5% agar (3 mL) and 100 μL of a shaking culture ($2.0 \times 10^9$ CFU/mL) of pathogenic bacteria were mixed and seeded on a TSA+ medium to prepare top agar. Cultures of 12 kinds of *Bacillus subtilis* strains (those possessed by CJ CheilJedang and commercial strains), each in an amount of 10 μL, were dropped on top of the prepared top agar, cultured at 30° C. for 18 hours, and the presence/absence of clear zones was observed. The antibacterial activity of commercially available *Bacillus subtilis* and complex phage was evaluated together.

TABLE 1

| Subjects for Antibacterial Evaluation | *Vibrio parahaemolyticus* |
|---|---|
| *Bacillus subtilis* 1 (CJBS-01) | ++++ |
| *Bacillus subtilis* 2 (CJBS-02) | + |
| *Bacillus subtilis* 3 (CJBS-03) | − |
| *Bacillus subtilis* 4 (CJBS-04) | − |
| *Bacillus subtilis* 5 (CJBS-05) | + |
| *Bacillus subtilis* 6 (CJBS-06) | − |
| *Bacillus subtilis* 7 (CJBS-07) | − |
| *Bacillus subtilis* 8 (CJBS-08) | − |
| *Bacillus subtilis* 9 (CJBS-09) | + |
| *Bacillus subtilis*10 (CJBS-10) | − |
| *Bacillus subtilis* 11 (CJBS-11) | − |
| *Bacillus subtilis* 12 (CJBS-12) | − |
| *Bacillus subtilis* (commercially purchased, Company A, Korea) | + |
| Complex phage | − |

++++: strong activity,
+: presence of activity,
−: no activity

As shown in Table 1 above, the *Bacillus subtilis* 1 microorganism (CJBS-01) showed the most excellent antibacterial effect in vitro against *Vibrio parahaemolyticus*, which causes AHPND. However, although the microorganism showed antibacterial activity in vitro against a particular pathogen, the antibacterial activity observed is simply an in vitro effect and it does not necessarily mean that the ingestion of *Vibrio parahaemolyticus* by an animal will be able to provide the animal with immunity or a preventive effect against the particular pathogen.

Accordingly, in the following experiments, it was examined whether the *Bacillus subtilis* 1 (CJBS-01) microorganism, when fed to shrimp, could lead to exhibition of an improvement in immunity and a disease preventive effect in the shrimp against the AHPND disease. Additionally, it was also examined whether the *Bacillus subtilis* 1 (CJBS-01) has an effect on weight gain and digestion rate.

The *Bacillus subtilis* 1 (CJBS-01) is a strain deposited to the Korean Culture Center of Microorganisms (KCCM) on Dec. 14, 2010, and was assigned Accession No. KCCM11143P.

Preparation Example 2. Preparation of *Bacillus subtilis*-Containing Feed Composition for Shrimp A feed composition containing the *Bacillus subtilis* 1 (Accession No. KCCM11143P, hereinafter "BS") selected in Preparation Example 1 was prepared.

Specifically, the compositions of Comparative Example 1 not containing *Bacillus subtilis*, Comparative Example 2 containing commercially available *Bacillus* species (i.e., a mixed preparation of three *Bacillus* species (*B. subtilis*, *B. pumilus*, and *B. licheniformis*)), and Example 1 containing the selected *Bacillus subtilis* 1 (BS) in an amount of $10^{10} \times$ 0.2 CFU/g were each mixed with fish oil and water, and prepared in the form of a pellet. The feed compositions of Comparative Examples 1 and 2 and Example 1 were dried at 25° C. for about 24 hours using a dryer and stored at −20° C. until subsequent experiments.

TABLE 2

| Ingredients (%) | Comparative Example 1 | Comparative Example 2 | Example 1 |
|---|---|---|---|
| Fish meal | 40 | 40 | 40 |
| SBM 44% South America | 12.81 | 12.81 | 12.81 |
| Squid liver powder | 10 | 10 | 10 |
| Wheat flour | 25.61 | 25.61 | 25.61 |
| Amygluten 110 | 3 | 3 | 3 |
| Fish oil A/C | 2 | 2 | 2 |
| Amino acid | 0.42 | 0.42 | 0.42 |
| Vitamin/Mineral premix | 5.96 | 5.96 | 5.96 |
| Rice bran | 0.2 | 0.18 | 0.00 |
| 3 Kinds of *Bacillus* Species ($10^{10} \times$ CFU/g) | 0.00 | 0.2 | 0.00 |
| BS ($10^{10} \times$ CFU/g) | 0.00 | 0.00 | 0.2 |
| BS + BP ($10^{10} \times$ CFU/g) | 0.00 | 0.00 | 0.00 |
| BS + BP + BL ($10^{10} \times$ CFU/g) | 0.00 | 0.00 | 0.00 |
| Chemical Composition (% dry matter) | | | |
| Moisture | 5.68 | 5.57 | 5.60 |
| Crude protein | 47.3 | 47.4 | 47.4 |
| Crude lipid | 7.31 | 7.47 | 7.49 |
| Crude ash | 6.01 | 6.18 | 6.12 |

Experimental Example 1. Evaluation of Preventive Effect of Feed Compositions Against AHPND 1-1. Preparation of Shrimp and Evaluation of Growth Rate Thirty whiteleg shrimp were prepared per water tank in a total of 40 water tanks. All of the experimental water tanks were equipped with air stones to maintain dissolved oxygen, and temperature of the water tanks was maintained in a range of 28° C. to 32° C. during the entire period of the experiment. The feed was fed 4 times a day with a limited supply (4% to 12% of fish weight).

The weight of the shrimp was measured every 2 weeks. The evaluation items and the equations for calculation related to growth rate and feed efficiency are as follows:

Weight Gain (%)=100×(final average body weight−initial average body weight)/average body weight Feed Conversion Rate (%)=amount of weight gain/amount of feed intake Daily Specific Growth Rate (% day$^{-1}$)=100×(log$_e$ final body weight−log$_e$ initial body weight)/days For the distribution of experimental feed, a completely randomized design was performed and the results of growth and analysis were statistically analyzed by one-way ANOVA using the SPSS Version 18.0 program. Significant differences in data values were compared between Duncan's multiple range test ($P<0.05$). The data was expressed as mean±SD and percentage data was calculated as arcsine transformed values and analyzed statistically.

TABLE 3

|  | Control Group 1 | Control Group 2 | BS Group 1 |
| --- | --- | --- | --- |
| IBW$^1$ (g) | 0.51 ± 0.01 | 0.51 ± 0.01 | 0.51 ± 0.01 |
| FBW$^2$ (g) | 3.49 ± 0.12$^{bc}$ | 3.80 ± 0.22$^{ab}$ | 3.86 ± 0.18$^a$ |
| WG$^3$ (%) | 592 ± 18.9$^c$ | 655 ± 39.3$^{ab}$ | 667 ± 31.9$^a$ |
| SGR$^4$ (%) | 6.04 ± 0.09$^b$ | 6.31 ± 0.16$^a$ | 6.37 ± 0.13$^a$ |
| FCR$^5$ | 1.30 ± 0.26 | 1.28 ± 0.09 | 1.19 ± 0.12 |
| Survival (%) | 80.0 ± 3.33 | 75.6 ± 6.94 | 71.1 ± 6.94 |

$^1$IBW: Initial body weight
$^2$FBW: Final body weight
$^3$WG: Weight gain (%) = [(final body weight − initial body weight)/initial body weight] × 100
$^4$SGR: Daily specific growth rate (% day$^{-1}$) = [(log$_e$ final body weight − log$_e$ initial body weight)/days] × 100
$^5$FCR: Feed conversion rate = dry feed fed/wet weight gain As shown in Table 3, as a result of feeding tests, it was confirmed that the BS Group 1, which was provided with the feed composition of Example 1 containing the *Bacillus subtilis* 1 (BS) selected in Preparation Example 1, exhibited a significantly higher growth rate, compared to Control Group 1 and Control Group 2, which were provided with each of the feed compositions of Comparative Example 1 and Comparative Example 2. Additionally, it was confirmed that the group provided with the feed composition of Example 1 had a significantly higher daily specific growth rate than the groups provided with each of the feed compositions of Comparative Example 1 and Comparative Example 2.

1-2. Test of *Vibrio parahaemolyticus* Attack on Shrimp

The test of *Vibrio parahaemolyticus* attack on shrimp was performed over a total of two divided tests. In the case of the *Vibrio* strain, AHPND (EMS)-causing strains isolated in Vietnam in 2013 were used for the tests. The attack test was carried out as follows: the feed compositions of Examples were fed to shrimp for two weeks, and then shrimp with the same weight (average weight: 2.32 g) were distributed into 4 replicates with 96 shrimps per group. The bacteria were cultured at 30° C. with 150 rpm for 24 hours using the TSB$^+$ medium, and a suspension of *Vibrio parahaemolyticus* (30 mL) was immersed into each of 20 acrylic water tanks (110 L, working volume: 72.5 L) at a concentration of 2×10$^9$ CFU (OD: 1.7). After the immersion, the survival and swimming status of the shrimp were confirmed every hour, and after 8 hours, 95% of the water was exchanged. The test feed was given three times a day (at 8:30, 13:30 and 18:30) in a divided dose in a restricted manner (10 to 12% of fish body weight), and the degree of mortality was observed for 70 hours. The results are shown in Table 4 below.

TABLE 4

| Treatment | Survival (%) Trial |
| --- | --- |
| Control Group 1 | 50.0 ± 16.0 |
| Control Group 2 | 49.0 ± 23.2 |
| BS Group 1 | 67.7 ± 28.9 |

As shown in Table 4 above, the BS Group 1, which was provided with the feed composition containing the *Bacillus subtilis* 1 (BS) selected in Preparation Example 1, exhibited a higher survival rate in the attack test of *Vibrio parahaemolyticus* against shrimp, compared to Control Group 1 and Control Group 2.

Additionally, as shown in FIG. 1, it was commonly observed in the above two tests that after the immersion of *Vibrio parahaemolyticus*, the movement of shrimp became slowed and they sat at the bottom of the water tank without swimming activity, and their feed intake was also not active. At 8 hours after immersion, rapid mortality of shrimp began to occur, and the survival rate of the BS Group 1 was shown to be higher compared to those of Control Group 1 or Control Group 2 by at least 17%.

1-3. Method of Sample Collection and Method of Histopathological Analysis

At each time-point of the initiation (before infection), intermediate time (infection), and completion of the attack test of *Vibrio parahaemolyticus* against shrimp, two shrimp per group were randomly selected and their hepatopancreases were extracted. Part of the extracted hepatopancreas was stored in ethyl alcohol (100%) for quantitative real-time PCR (qPCR) analysis, and another part was fixed in Davidson's fixative for 24 hours and then stored in ethyl alcohol (70%) for histopathological analysis.

More specifically, the histopathological analysis was performed by the following method.

To minimize the damage of the extracted hepatopancreas tissue, immediately after the sampling in each water tank, Davidson's fixative was injected into the hepatopancreas of shrimp using a 1 mL syringe and the hepatopancreas was extracted. Then, each extracted hepatopancreas was fixed in a 1.5 mL Eppendorf tube containing Davidson's fixative for 24 hours, stored in ethyl alcohol (70%), and used for analysis. Upon completion of fixing, the organs were trimmed to a thickness of about 2 mm to about 3 mm in size to be suitable for the preparation of tissue specimens and inserted into a cassette, and their tissues were treated for 13 hours. These tissues were thinly cut to a thickness of about 4 μm, and the resulting specimens were collected using a brush, attached to each slide without any wrinkles, placed in the air for about 5 minutes, and then subjected to H&E staining. After completing the staining, the slides were photographed under 200× magnification with a professional program for use in microscopes (TCapture, Tucen Photonics) using a phase contrast microscope (BX50, Olympus). Then, qPCR analysis was performed with regard to the amount of AHPND toxin present in the sampled hepatopancreas.

Figure 2:
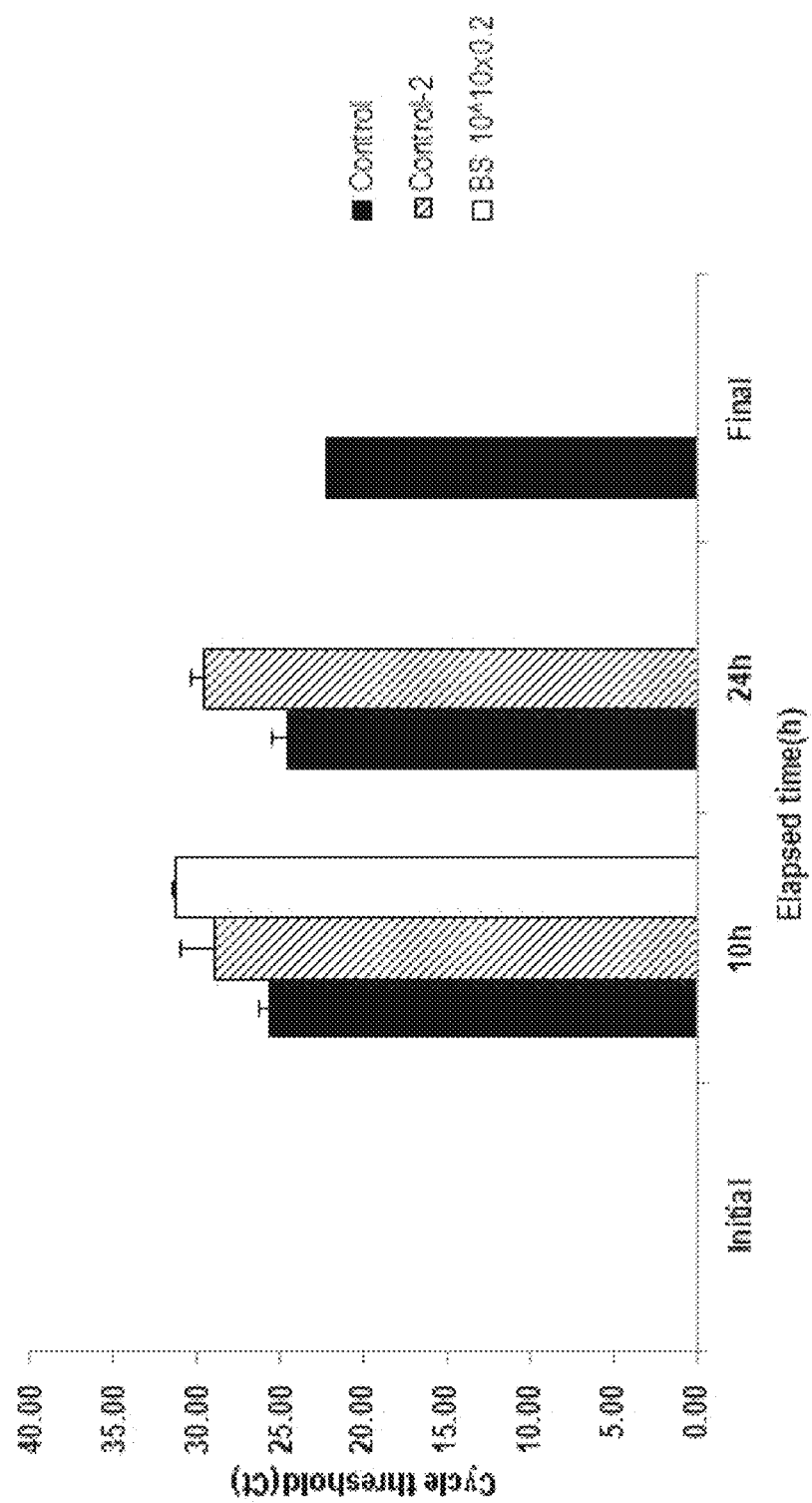
FIG. 2 is a graph showing the analysis of the AHPND content in the shrimp hepatopancreas.

The results are shown in FIG. 2, in which the lower Ct value indicates a higher amount of toxin.

In the hepatopancreas sampled at the time-point before the attack test (i.e., 0 h), no AHPND toxin was detected in all of the groups, whereas in the hepatopancreas sampled at the 10 hour time-point of the attack test (i.e., 10 h; when the number of dead subjects was highest), the AHPND toxin was detected in all of the samples. However, BS Group 1, which was provided with the feed composition containing the *Bacillus subtilis* according to the present disclosure, showed a significantly higher Ct value compared to Control Group 1 and Control Group 2, and in the hepatopancreas sampled at the 24 hour time-point of the attack test, the lowest level of AHPND toxin was detected in the BS Group 1. Additionally, at the termination time-point of the attack test (i.e., 193 h), the AHPND toxin was not detected in BS Group 1 and Control Group 2.

Figure 3:
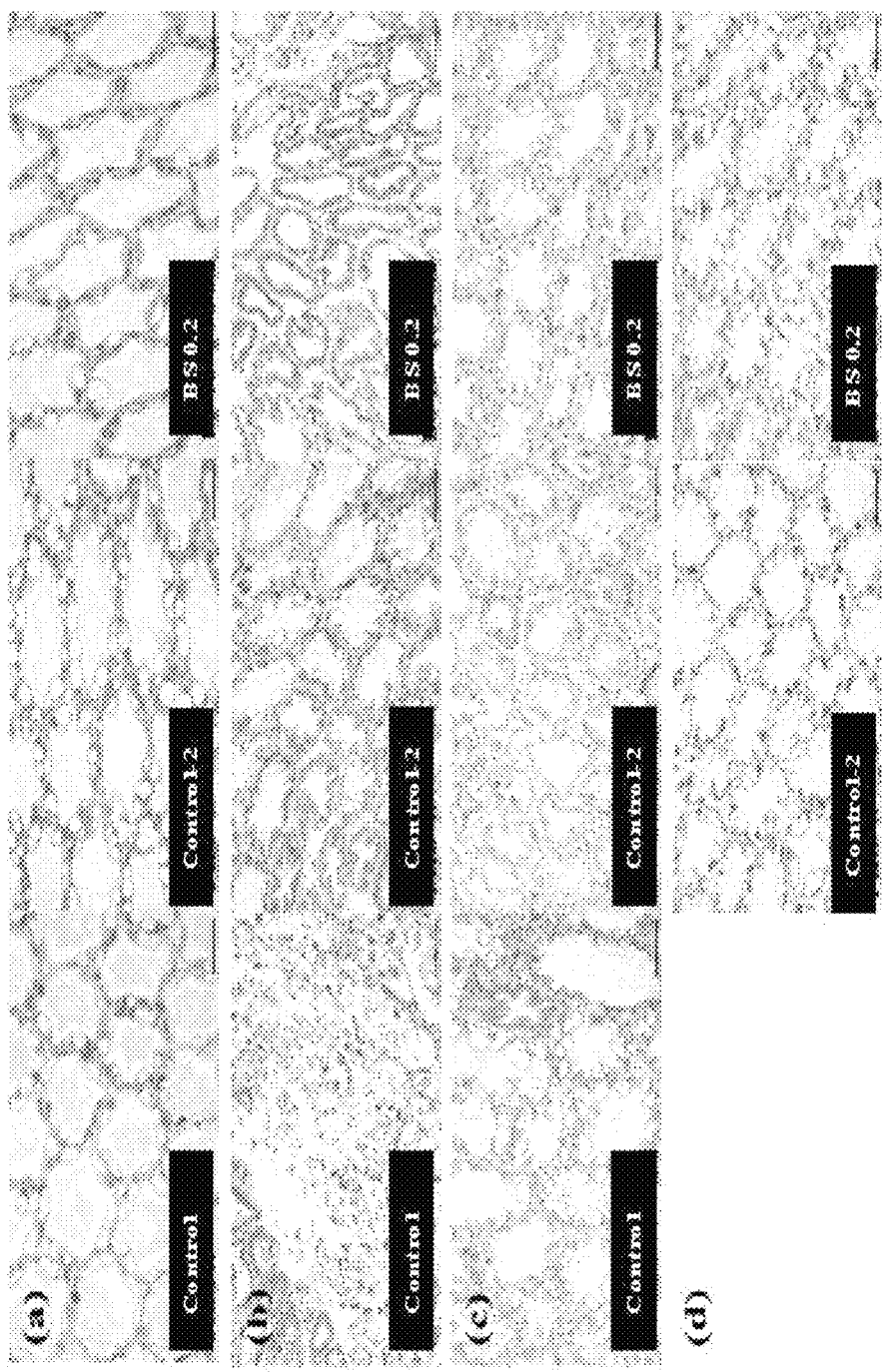
FIG. 3 is images showing the pathological features of the shrimp hepatopancreas.

Additionally, the results of histopathological analysis of the hepatopancreas are shown in FIG. 3.

In the hepatopancreas sampled at the time-point before the attack test (i.e., 0 h), abnormal tissues were observed in all of the groups. In the hepatopancreas sampled at the 10 hour time-point, the damage level was shown to be most severe in Control Group 1, and progress of tissue necrosis was observed in BS Group 1 and Control Group 2. In the hepatopancreas sampled at the 24 hour time-point, inflammation was observed rather than the tissue necrosis due to the AHPND toxin. In the hepatopancreas sampled at the termination time-point of the attack test (i.e., 193 h), the sampling was not possible due to the occurrence of 100% death at the time-point of 37 h in Control Group 1, whereas some inflammatory cells were observed in the BS Group 1 and Control Group 2.

From the above results, it was confirmed that the feed composition containing the *Bacillus subtilis* according to the present disclosure can not only improve the disease resistance of shrimp to *Vibrio parahaemolyticus* infection, but can also significantly reduce the amount of AHPND toxin in the hepatopancreas of shrimp.

Experimental Example 2. Evaluation of Growth Rate and Immunity According to Concentration of *Bacillus subtilis*, *Bacillus Pumilus*, and *Bacillus licheniformis*

Considering the results in Preparation Example 2, feed compositions (Examples 1 to 5) containing various concentrations of each of the *Bacillus subtilis* 1 (KCCM11143P, hereinafter "BS") selected in Preparation Example 1, *Bacillus pumilus* (KCCM11144P, hereinafter "BP"), and *Bacillus licheniformis* (KCCM11270P, hereinafter "BL") were prepared. The results are shown in Table 5 below.

TABLE 5

| Ingredients (%) | Comparative Example 1 | Comparative Example 2 | Example 1 | Example 2 | Example 3 | Example 4 | Example 5 |
|---|---|---|---|---|---|---|---|
| Fish meal | 40 | 40 | 40 | 40 | 40 | 40 | 40 |
| SBM 44% South America | 12.81 | 12.81 | 12.81 | 12.81 | 12.81 | 12.81 | 12.81 |
| Squid liver powder | 10 | 10 | 10 | 10 | 10 | 10 | 10 |
| Wheat flour | 25.61 | 25.61 | 25.61 | 25.61 | 25.61 | 25.61 | 25.61 |
| Amygluten 110 | 3 | 3 | 3 | 3 | 3 | 3 | 3 |
| Fish oil A/C | 2 | 2 | 2 | 2 | 2 | 2 | 2 |
| Amino acid | 0.42 | 0.42 | 0.42 | 0.42 | 0.42 | 0.42 | 0.42 |
| Vitamin/Mineral premix | 5.96 | 5.96 | 5.96 | 5.96 | 5.96 | 5.96 | 5.96 |
| Rice bran | 0.2 | 0.18 | 0.00 | 0.00 | 0.00 | 0.00 | 0.00 |
| BS + BP + BL ($10^{10}$ × CFU/g) | 0.00 | 0.2 | 0.00 | 0.00 | 0.00 | 0.00 | 0.00 |
| BS ($10^{10}$ × CFU/g) | 0.00 | 0.00 | 0.2 | 0.1 | 0.00 | 0.00 | 0.00 |
| BS + BP ($10^{10}$ × CFU/g) | 0.00 | 0.00 | 0.00 | 0.00 | 0.1 | 0.2 | 0.00 |
| BS + BP + BL ($10^9$ × CFU/g) | 0.00 | 0.00 | 0.00 | 0.00 | 0.00 | 0.00 | 0.2 |
| Chemical composition (%, dry matter) | | | | | | | |
| Moisture | 5.59 | 5.80 | 5.78 | 5.71 | 5.71 | 5.71 | 5.71 |
| Crude protein | 47.3 | 48.6 | 49.2 | 48.9 | 48.1 | 48.5 | 48.5 |
| Crude lipid | 7.74 | 7.71 | 7.73 | 7.70 | 7.70 | 7.72 | 7.70 |
| Crude ash | 6.12 | 6.12 | 6.20 | 6.10 | 6.10 | 6.12 | 6.11 |

The composition of each group in Table 5 was prepared by adding fish oil and water, mixing followed by pelletizing. The composition of each group in Table 5 was dried at 25° C. for about 24 hours using a dryer and stored at −20° C. until subsequent experiments.

2-1. Preparation of Shrimp and Evaluation of Growth Rate

Five whiteleg shrimp were prepared per water tank in a total of 280 water tanks. All of the experimental water tanks were equipped with air stones to maintain dissolved oxygen, and temperature of the water tanks was maintained in a range of 28° C. to 32° C. during the entire period of the experiment. The feed was fed 4 times a day for 8 weeks with a limited supply (6% to 12% of fish weight, initial body weight: 0.14 g).

The weight of the shrimp was measured every 2 weeks. The evaluation items and the equations for calculation related to growth rate and feed efficiency are as follows:

Weight Gain (%)=100×(final average body weight−initial average body weight)/average body weight Feed Conversion Rate (%)=amount of weight gain/amount of feed intake Daily Specific Growth Rate (% day$^{-1}$)=100×(log$_e$ final body weight−log$_e$ initial body weight)/days The results are shown in Table 6 below.

and 26.1%, respectively. The feed efficiencies of BS+BP Group 1, BS+BP Group 2, and BS+BP+BL Group 1 were increased compared to that of Control Group 1, by 11.1%, 20.9%, and 13.1%, respectively. However, there was no significant difference in the survival rate of shrimp in all of the groups.

2-2. Sample Collection

Test shrimp were weighed every 2 weeks and all of the test shrimp were fasted to reduce the stress of the shrimp 18 hours before the measurement.

After the measurement of final weight, 7 shrimp were randomly selected from each water tank and anesthetized in ice water, and hemolymph was collected using a syringe treated with Alsever's solution. The collected hemolymph was used for the analysis of nitroblue tetrazolium activity (NBT), and the samples in which sera were separated using a centrifuge (800 g, 10 min, 4° C.) were used for the analysis of non-specific immunity.

With regard to the collection of shrimp feces for digestion rate analysis, the feed and impurities remaining in the water tanks were cleaned by siphoning and water exchange after 30 minutes of feeding, and 3 hours thereafter, the feces being

TABLE 6

|  | Control Group 1 | Control Group 2 | BS Group 1 | BS Group 2 | BS + BP Group 1 | BS + BP Group 2 | BS + BP + BL Group 1 |
|---|---|---|---|---|---|---|---|
| IBW[1] (g) | 0.14 ± 0.00 | 0.14 ± 0.00 | 0.14 ± 0.00 | 0.14 ± 0.00 | 0.14 ± 0.00 | 0.14 ± 0.00 | 0.14 ± 0.00 |
| FBW[2] (g) | 10.2 ± 0.69$^b$ | 11.3 ± 0.45$^a$ | 11.9 ± 0.43$^a$ | 11.5 ± 0.60$^a$ | 11.0 ± 0.91 | 11.8 ± 0.47 | 11.1 ± 0.36 |
| WG[3] (%) | 7029 ± 506$^b$ | 7969 ± 413$^a$ | 8381 ± 356$^a$ | 8085 ± 464$^a$ | 7818 ± 772 | 8151 ± 202 | 7859 ± 303 |
| SGR[4] (%) | 7.62 ± 0.13$^b$ | 7.84 ± 0.09$^a$ | 7.93 ± 0.07$^a$ | 7.86 ± 0.10$^a$ | 7.80 ± 0.17 | 7.88 ± 0.04 | 7.81 ± 0.07 |
| FCR[5] | 1.53 ± 0.04$^c$ | 1.21 ± 0.09$^{ab}$ | 1.11 ± 0.22$^a$ | 1.13 ± 0.12$^a$ | 1.36 ± 0.06 | 1.21 ± 0.05 | 1.33 ± 0.08 |
| Survival (%) | 90.7 ± 6.11 | 92.0 ± 4.00 | 84.0 ± 17.4 | 88.0 ± 8.00 | 88.0 ± 4.00 | 85.3 ± 4.62 | 86.7 ± 6.11 |

* ($P < 0.05$)
[1]IBW: Initial body weight
[2]FBW: Final body weight
[3]WG: Weight gain (%) = [(final body weight − initial body weight)/initial body weight] × 100
[4]SGR: Daily specific growth rate (% day$^{-1}$) = [(log$_e$ final body weight − log$_e$ initial body weight)/days] × 100
[5]FCR: Feed conversion rate = dry feed fed/wet weight gain As shown in Table 6 and FIG. 4, all groups of shrimp fed for 8 weeks showed an increase of growth rate over 7,000% compared to those before feeding. In particular, the final average body weight of BS Group 1 (provided with the feed composition of Example 1) and the final average body weight of BS Group 2 (provided with the feed composition of Example 2) were greater than that of Control Group 1, by 15.7% and 16.7%, respectively. The final average body weight of BS+BP Group 1 (provided with the feed composition of Example 3), the final average body weight of BS+BP Group 2 (provided with the feed composition of Example 4), and the final average body weight of BS+BP+BL Group 1 (provided with the feed composition of Example 5) were increased compared to that of Control Group 1, by 7.8%, 15.6%, and 8.8%, respectively. Additionally, with regard to daily specific growth rate, BS Group 1 and BS Group 2 showed increased values compared to Control Group 1, by 3.4% and 4.1%, respectively. The daily specific growth rates of BS+BP Group 1, BS+BP Group 2, and BS+BP+BL Group 1 were increased compared to that of Control Group 1, by 2.4%, 3.4%, and 2.5%, respectively. The feed efficiencies of BS Group 1 and BS Group 2 were improved compared to that of Control Group 1, by 27.5% excreted were collected using a siphon. The collected samples were washed with distilled water, filtered through a filter paper, and stored in a −40° C. low-temperature freezer until use as a sample for analysis.

2-3. Statistical Analysis

For the distribution of experimental feed, a completely randomized design was performed and the results of growth and analysis were statistically analyzed by one-way ANOVA using the SPSS Version 18.0 program. Significant differences in data values were compared between Duncan's multiple range test ($P<0.05$). The data was expressed as mean±SD and percentage data was calculated as arcsine transformed values and analyzed statistically.

2-4. Analysis of Common Ingredients

The test feed and the common ingredients of the feces were analyzed according to the AOAC (2005) method; the moisture contents by an atmospheric-pressure heating-drying method (125° C., 3 h) (Kejltec system 2300, Sweden); crude ash by a direct incineration method (550° C., 4 h); crude proteins by an automated crude protein analyzer (Kejltec system 2300, Sweden); and crude lipids by the method of Folch et al. (1957). The results are shown in Table 7 below.

TABLE 7

| | Control Group 1 | Control Group 2 | BS Group 1 | BS Group 2 | BS + BP Group 1 | BS + BP Group 2 | BS + BP + BL Group 1 |
|---|---|---|---|---|---|---|---|
| Dry Matters | 24.9 ± 0.35 | 24.5 ± 0.10 | 23.7 ± 0.39 | 23.7 ± 0.35 | 25.1 ± 0.36 | 24.3 ± 0.23 | 24.3 ± 0.16 |
| Crude Ash | 12.9 ± 2.34 | 12.8 ± 0.12 | 12.3 ± 0.33 | 14.5 ± 0.22 | 14.8 ± 3.47 | 13.9 ± 1.46 | 14.6 ± 3.60 |
| Crude Proteins | 76.5 ± 3.46$^b$ | 82.0 ± 1.67$^a$ | 84.3 ± 2.85$^a$ | 83.9 ± 2.31$^a$ | 79.4 ± 2.23$^{ab}$ | 82.0 ± 3.58$^a$ | 81.8 ± 1.52$^a$ |
| Crude Lipids | 5.37 ± 0.96 | 5.45 ± 1.15 | 5.09 ± 0.28 | 5.26 ± 1.05 | 5.29 ± 0.12 | 5.40 ± 0.53 | 5.59 ± 0.73 |

(*P < 0.05)

As shown in Table 7, with regard to the contents of crude ash and crude lipids, there were no significant differences among the groups. However, the content of the crude protein in BS Group 2 was significantly higher compared to those of Control Group 1 and Control Group 2. That is, it was confirmed that when the feed compositions according to the present disclosure are provided to shrimp, the protein content of shrimp can be increased.

2-5. Analysis Related to Non-Specific Immunity 2-5-1. Analysis of Nitroblue Tetrazolium (NBT) Activity The amount of oxidative radical production by neutrophils during respiratory explosion was determined using the analysis method of Zhang et al. (2013).

Specifically, first, hemolymph (50 μL) was mixed with 200 μL of the Hank's balanced salt solution (HBSS) and allowed to react at 25° C. After 30 minutes, 100 μL of zymosan (0.1% Hank's solution) was added thereto and reacted at 37° C. for 2 hours. NBT solution (0.3%) was added thereto in an amount of 100 μL each time and reacted at 37° C. for 2 hours. 100% methanol (600 μL) was added thereto and the mixture was centrifuged at a rate of 6,500 rpm for 10 minutes. The supernatant was discarded and the pellet was washed 3 times with 70% methanol (100 μL) and dried for 5 minutes. Then, 2 M KOH (700 μL) and DMSO (800 μL) were added thereto, and the absorbance of the resultant was measured at 620 nm.

2-5-2. Analysis of Glutathione Peroxidase (GPx) Activity

The GPx activity in serum was analyzed using the GPx kit (Biovision, Inc. California).

Specifically, as the cumene hydroperoxide, a reaction mixture in which peroxide substrate (ROOH), glutathione reductase (GSSG-R), and reduced b-nicotinamide adenine denucleotide phosphate (NADPH) were mixed was used. First, a hemolymph sample (50 μL) was added into a microplater, and a reaction mixture (40 μL) was added thereto and reacted. Then, cumene hydroperoxide (10 μL) was added thereto, and after 5 minutes, the absorbance of the resultant was measured at 340 nm. The GPx activity was calculated as nmol/min/mL.

2-5-3. Analysis of Lysozyme Activity

The analysis of lysozyme activity was analyzed based on the method of Swain et al. (2007).

Specifically, lysozyme, which is an antibacterial enzyme involved in nonspecific (innate) immune responses, is an enzyme that exhibits antibacterial activity against various kinds of bacteria in a non-specific manner, rather than in a specific manner for a specific bacterium.

The antibacterial mechanism against pathogenic bacteria is the antibacterial action that hydrolyzes β-1,4-glucosidic bonds of peptidoglycan, which is a constituent of bacterial cell walls, thereby destroying bacterial cell walls. Lysozyme is especially effective against gram-positive bacteria. Based on such a mechanism, lysozyme activity is widely used for analysis to measure non-specific immune responses in shrimp including fish. When immunostimulators (e.g., ascorbic acid, β-glucan, probiotics, etc.) are added to the shrimp feed, it is possible to confirm the increased lysozyme activity in the hemolymph and tissues of shrimp, and these results are interpreted as a result of an increase in a non-specific immune response or improvement in the immunity of fish (shrimp).

2-5-4. Analysis of Phenoloxidase (PO) Activity

The phenoloxidase (PO) activity was analyzed based on the method of Hernandez-Lopez et al. (1996).

Specifically, phenoloxidase, which is an enzyme that has an important role in the defense mechanism of the *Crustacea*, is present in the form of prophenoloxidase in blood cells and activated by the prophenoloxidase activating system. The activated phenoloxidase produces opsonin, which promotes the phagocytosis of the blood cells and the coating action on the foreign antigen and participates in the blood clotting reaction. Accordingly, the phenoloxidase activity within the hemolymph is used as an important index of the innate immunity of shrimp.

2-5-5. Analysis of Superoxide Dismutase (SOD) Activity

The SOD activity was analyzed using the SOD assay kit (Sigma-Aldrich, 19160, St. Louis, USA).

Specifically, a radical detector (20 μL) was added into a 96-well plate, and each blood sample (20 μL) was added to each well. Then, xanthine oxidase (20 μL) was added thereto and reacted for 20 minutes. The absorbance of the resultant was measured at 450 nm using the Microplate Reader (Thermo).

2-5-6. Analysis of Antiprotease Activity

The antiprotease activity within the hemolymph was analyzed using the analysis method of Ellis (1990).

Specifically, hemolymph (20 μL) and standard trypsin solution (20 μL; Type II-S, from porcine pancreas, Sigma-Aldrich, A2765, St. Louis, USA) were mixed and cultured at 22° C. for 10 minutes. Phosphate buffer (200 μL; 0.1 M, pH 7.0) and azocasein (2%) (250 μL; Sigma-Aldrich) were added thereto, cultured at 22° C. for 1 hour, and trichloroacetic acid (500 μL; 10%) (TCA) was again added thereto, and cultured at 22° C. for 30 minutes. The cultured solution was centrifuged (6000 g, 5 min), and the resultant (100 μL) was seeded into a 96-well plate, and 1 N NaOH (100 μL) was added thereto, and the absorbance of the resultant was measured at 430 nm using the Microplate Reader.

The results of Experimental Examples 2-5-1 to 2-5-6 in which the non-specific immunological analysis was performed are shown in Table 8 below.

TABLE 8

|  | Control Group 1 | Control Group 2 | BS Group 1 | BS Group 2 | BS + BP Group 1 | BS + BP Group 2 | BS + BP + BL Group 1 |
|---|---|---|---|---|---|---|---|
| NBT[1] | $1.65 \pm 0.15^c$ | $1.72 \pm 0.08^{bc}$ | $1.85 \pm 0.03^{ab}$ | $1.79 \pm 0.13^{ab}$ | $1.89 \pm 0.03^a$ | $1.86 \pm 0.03^{ab}$ | $1.83 \pm 0.06^{ab}$ |
| PO[2] | $0.213 \pm 0.008^b$ | $0.249 \pm 0.031^a$ | $0.254 \pm 0.015^a$ | $0.249 \pm 0.009^a$ | $0.270 \pm 0.023^a$ | $0.250 \pm 0.011^a$ | $0.252 \pm 0.006^a$ |
| Antiprotease[3] | $31.6 \pm 2.4^b$ | $35.8 \pm 0.3^a$ | $36.6 \pm 1.8^a$ | $36.1 \pm 3.4^a$ | $34.8 \pm 1.2^a$ | $36.1 \pm 2.1^a$ | $36.5 \pm 2.0^a$ |
| Lysozyme[4] | $6.40 \pm 1.04^b$ | $8.57 \pm 0.50^a$ | $8.43 \pm 0.98^a$ | $8.08 \pm 1.26^{ab}$ | $8.02 \pm 1.21^{ab}$ | $7.89 \pm 1.02^{ab}$ | $7.58 \pm 1.70^{ab}$ |
| SOD[5] | $67.3 \pm 4.6^b$ | $73.1 \pm 3.3^{ab}$ | $74.8 \pm 4.6^{ab}$ | $72.8 \pm 7.7^{ab}$ | $77.2 \pm 6.0^a$ | $70.7 \pm 4.1^{ab}$ | $74.1 \pm 8.3^{ab}$ |
| GPx[6] | $28.5 \pm 1.9^d$ | $32.7 \pm 2.4^c$ | $36.4 \pm 1.7^{abc}$ | $36.7 \pm 2.3^a$ | $34.3 \pm 2.6^{abc}$ | $32.8 \pm 3.3^{bc}$ | $36.6 \pm 2.3^{ab}$ |

(*P < 0.05)
[1]Nitroblue tetrazolium; phagocytic activity (absorbance)
[2]Phenoloxidase activity (absorbance)
[3]Antiprotease (% inhibition)
[4]Lysozyme activity ($\mu g\ mL^{-1}$)
[5]Superoxide dismutase (% inhibition)
[6]Glutathione peroxidase ($mU\ mL^{-1}$)

As shown in Table 8 and FIG. 5, with regard to the NBT activity and PO activity, all of BS Group 1, BS Group 2, BS+BP Group 1, BS+BP Group 2, and BS+BP+BL Group 1 showed significantly higher values, compared to Control Group 1 and Control Group 2; and in particular, in the case of PO activity, BS Group 1 showed a higher value compared to Control Group 1 by 26.8%. With regard to the antiprotease activity, all of BS Group 1, BS Group 2, BS+BP Group 2, and BS+BP+BL Group 1 showed significantly higher values, compared to Control Group 1 and Control Group 2; and in particular, BS Group 1 showed a higher value compared to Control Group 1 by 15.8%. With regard to the lysozyme activity and SOD activity, all of BS Group 1, BS Group 2, BS+BP Group 1, BS+BP Group 2, and BS+BP+BL Group 1 were shown to be significantly higher compared to that of Control Group 1. With regard to the GPx activity, all of BS Group 1, BS Group 2, BS+BP Group 1, BS+BP Group 2, and BS+BP+BL Group 1 showed significantly higher values, compared to Control Group 1 and Control Group 2; and in particular, BS Group 1 and BS Group 2 showed higher values compared to Control Group 1 by 27.7% and 28.8%, respectively.

2-6. Analysis of Water Quality and Zero Water Exchange Experiment

During 8 weeks of the feeding experiment, the samples of culture water were collected from each water tank once every 5 days. The samples were collected from the same location in each tank, and the level of dissolved oxygen (DO), salinity, pH, and the concentration of ammonia ($NH_4^+$) were measured. The DO was measured by a Thermo Scientific Orion Star A216 Benchtop Meter (Thermo Scientific), the salinity was measured by a Master Refractometer (ATAGO). The pH was measured by a Seven Compact (METTLER TOLEDO), and the concentration of $NH_4^+$ was analyzed by the method according to Verdouw et al. (1978).

Twelve whiteleg shrimp (*L. vannamei*) having an average weight of 2.87 (±0.08) g were randomly placed in each 96 L water tank for a total of 14 water tanks using a zero water change method. There were two replicates for each test group, and the shrimp were given a test feed 10% of their body weight four times a day in a divided dose (at 08:30, 12:00, 15:30, and 19:00). According to Verdouw et al. (1978), the water samples were collected once a day, and the concentration of total ammonia in the water samples was measured for 10 days. The results are shown in Table 9

TABLE 9

|  | DO mg $L^{-1}$ | pH | $NH_4^+$ mg $L^{-1}$ |
|---|---|---|---|
| Mean | 6.85 | 7.10 | 0.102 |
| Max | 7.21 | 6.78 | 0.154 |
| Min | 6.39 | 6.48 | 0.035 |

Figure 6:
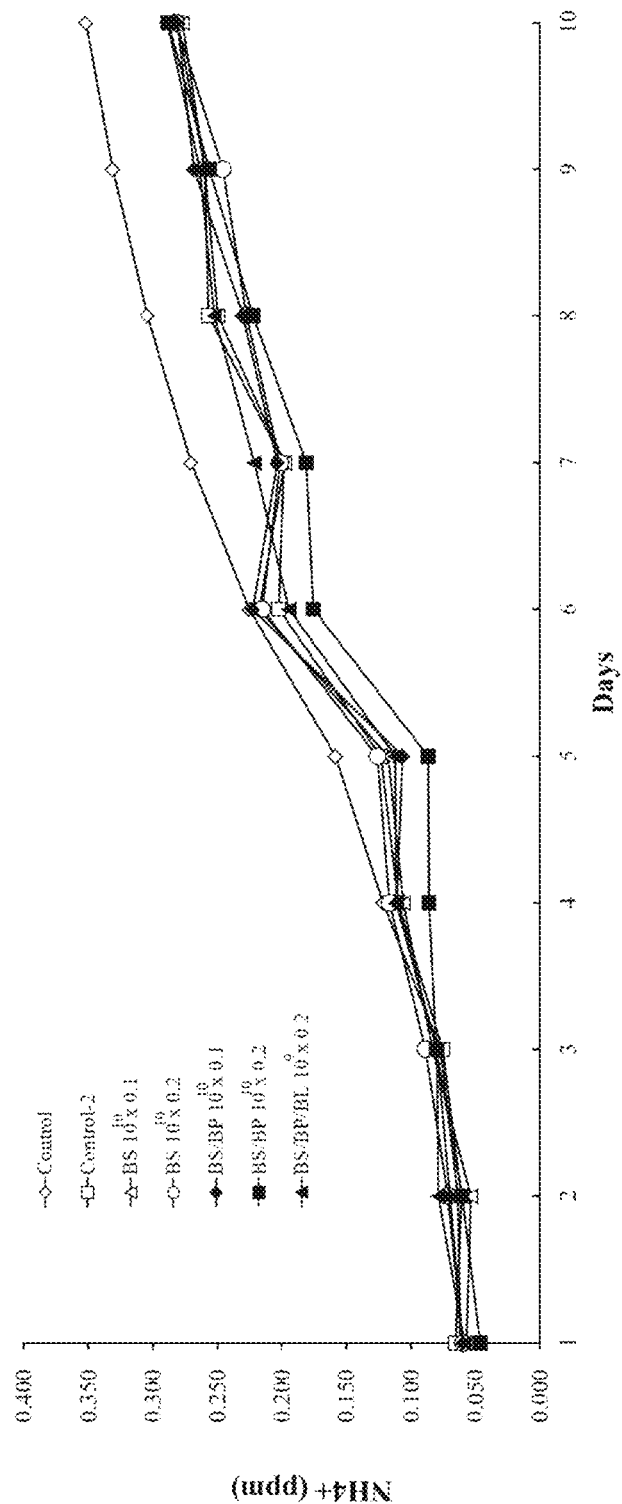
FIG. 6 is a graph showing the results of analysis of water quality in the breeding water with zero water exchange.

As shown in Table 9 and FIG. 6, interestingly, it was found that from day 7, all of the test groups began to show a lower total ammonia concentration than the control group, and that on day 10, all of the test groups showed a significantly lower ammonia concentration than the control group.

2-7. Analysis of Digestibility 2-7-1. Analysis of Indicator ($Cr_2O_3$)

In order to analyze the chromium oxide content in the test feed and the powders, the method according to Divakaran et al. (2002) was used.

Specifically, the test feed and the powder samples were subjected to ashing for 4 hours in an ashing furnace (550° C.), and the obtained samples were used for the analysis. First, in order to oxidize chromium oxide to a monochromate form, 5 mg to 10 mg of the powder samples was weighed and transferred to a glass test tube. 4 mL of perchloric reagent ($HClO_4$) was added to the glass test tube containing the sample. The perchloric reagent (70%) was prepared by mixing 200 mL of nitric acid in 100 mL of distilled water, cooling the mixture and then mixing 200 mL of 70% perchloric acid thereto. The glass test tube containing the sample and the perchloric reagent was placed in a heating plate, heated at 300° C. for 15 minutes, and then cooled to room temperature. The pretreated sample was transferred to a 50 mL glass flask and quantified to 25 mL with triple-distilled water. Thereafter, the absorbance was measured at 350 nm using a spectrophotometer (Beckman DU-730). The measured absorbance was used to calculate the chromium oxide content of the sample using a standard equation prepared from a pretreated standard solution as in the sample analysis.

2-7-2. Analysis of Dry Matter and Protein Digestibility

The dry matter and protein digestibility of the test feed were calculated by the following method:

ADC of dry matter (%)=100−100×(% $Cr_2O_3$ in diet/% $Cr_2O_3$ in feces);

ADC of protein (%)=100−100×(% $Cr_2O_3$ in diet/% $Cr_2O_3$ in feces)×(% protein in feces/% protein in diet)

The results of the digestibility analysis carried out at the end of the feeding experiment are shown in Table 10.

TABLE 10

| | Control Group 1 | Control Group 2 | BS Group 1 | BS Group 2 | BS + BP Group 1 | BS + BP Group 2 | BS + BP + BL Group 1 |
|---|---|---|---|---|---|---|---|
| ADCd (%)[1] | 85.6 ± 0.7$^c$ | 87.4 ± 0.6$^{ab}$ | 87.9 ± 0.4$^a$ | 86.9 ± 0.5$^b$ | 87.7 ± 0.3$^{ab}$ | 87.9 ± 0.3$^a$ | 88.1 ± 0.4$^a$ |
| ADCp (%)[2] | 93.5 ± 0.3$^b$ | 95.0 ± 0.2$^a$ | 95.2 ± 0.2$^a$ | 94.8 ± 0.2$^a$ | 95.0 ± 0.1$^a$ | 95.1 ± 0.1$^a$ | 95.1 ± 0.2$^a$ |

Values are mean of triplicate groups and presented as mean ± SD. Values with different superscripts in the same column are significantly different (P < 0.05).
[1]Apparent digestibility coefficient of dry matter
[2]Apparent digestibility coefficient of protein As shown in Table 10, all of the test groups showed significantly higher dry matter digestibility and protein digestibility than the control groups.

Preparation Example 3. Preparation of Shrimp Feed Composition Including *Bacillus subtilis*, *Bacillus pumilus*, and *Bacillus licheniformis*

Feed compositions including *Bacillus subtilis* 1 (Accession No. KCCM11143P, hereinafter referred to as 'BS'), *Bacillus pumilus* (Accession No. KCCM11144P, hereinafter referred to as 'BP''), and *Bacillus licheniformis* (hereinafter referred to as 'BL') selected in Preparation Example 1 were prepared.

Specifically, the composition of Comparative Example 1 not containing the strains of *Bacillus* species, the composition of Comparative Example 3 containing $10^9 \times 0.2$ CFU/g of BS, the composition of Comparative Example 4 containing $10^{10} \times 0.2$ CFU/g of BS, the composition of Example 5 containing $10^9 \times 0.2$ CFU/g of BS, BP, and BL, and the composition of Example 6 containing $10^{10} \times 0.2$ CFU/g of BS, BP, and BL were prepared in the form of pellet by adding fish oil and water and mixing the same. The feed compositions of Comparative Examples 1, 3, and 4, and Examples 5 and 6 were dried at 25° C. for about 24 hours using a dryer and stored at −20° C. until the experiment.

TABLE 11

| Ingredients (%) | Comparative Example 1 | Comparative Example 3 | Comparative Example 4 | Example 5 | Example 6 |
|---|---|---|---|---|---|
| Fish meal | 40 | 40 | 40 | 40 | 40 |
| SBM 44% South America | 12.81 | 12.81 | 12.81 | 12.81 | 12.81 |
| Squid liver powder | 10 | 10 | 10 | 10 | 10 |
| Wheat flour | 25.61 | 25.61 | 25.61 | 25.61 | 25.61 |
| Amygluten 110 | 3 | 3 | 3 | 3 | 3 |
| Fish oil A/C | 2 | 2 | 2 | 2 | 2 |
| Amino acid | 0.42 | 0.42 | 0.42 | 0.42 | 0.42 |
| Vitamin/Mineral premix | 5.96 | 5.96 | 5.96 | 5.96 | 5.96 |
| Rice bran | 0.2 | 0.2 | 0.2 | 0.18 | 0.00 |
| BS ($10^9 \times$ CFU/g) | 0.00 | 0.2 | 0.00 | 0.00 | 0.00 |
| BS ($10^{10} \times$ CFU/g) | 0.00 | 0.00 | 0.2 | 0.00 | 0.00 |
| BS + BP + BL ($10^9 \times$ CFU/g) | 0.00 | 0.00 | 0.00 | 0.2 | 0.00 |
| BS + BP + BL ($10^{10} \times$ CFU/g) | 0.00 | 0.00 | 0.00 | 0.00 | 0.2 |
| Chemical composition (% dry matter) | | | | | |
| Moisture | 5.68 | 5.61 | 5.60 | 5.71 | 5.71 |
| Crude protein | 47.3 | 47.4 | 47.4 | 48.5 | 48.5 |
| Crude lipid | 7.31 | 7.48 | 7.49 | 7.70 | 7.70 |
| Crude ash | 6.01 | 6.10 | 6.12 | 6.11 | 6.11 |

Experimental Example 3. Evaluation of Preventive Effect of Feed Composition on AHPND 3-1. Preparation of Shrimp Thirty whiteleg shrimp were prepared in each water tank for a total of 40 water tanks. All water tanks were equipped with an air stone to maintain dissolved oxygen, and the water temperature for feeding was maintained in the range of 28° C. to 32° C. throughout the entire experiment. The feed was given 4 times a day in a restricted manner (4% to 12% of fish body weight).

3-2. Attack Test of *Vibrio parahaemolyticus*

In order to confirm antibacterial activity of the feed compositions including *Bacillus subtilis*, *Bacillus pumilus*, and *Bacillus licheniformis*, the attack test was carried out once such that the shrimp were attacked by *Vibrio parahaemolyticus*. In the case of the *Vibrio* strain, AHPND (EMS)-induced strains isolated from Vietnam in 2013 were used for the test. The attack test was carried out as follows: the feed compositions of the Examples were fed to shrimp for 4 weeks, and then the shrimp with the same weight (average weight: 2.30 g) were distributed into 4 replicates with 96 shrimp per group. The bacteria were cultured at 30° C. at 150 rpm for 24 hours using a TSB$^+$ medium, and a suspension of *Vibrio parahaemolyticus* was immersed at a concentration of $6.3 \times 10^5$ CFU/mL per tank. After the immersion, the survival of shrimp and their swimming status were confirmed every hour, and after 8 hours, the 95% of the water was exchanged. The test feed was given three times a day (at 8:30, 13:30, and 18:30) in a divided dose in a restricted manner (10% to 12% of fish body weight), and the degree of mortality was observed for 70 hours. The results are shown in Table 12 below.

TABLE 12

| Treatment | Survival (%) Trial |
|---|---|
| Control Group 1 | 0.00 ± 0.00 |
| BS Group 3 | 8.93 ± 10.7 |
| BS Group 4 | 6.90 ± 5.45 |
| BS + BP + BL Group 1 | 15.6 ± 11.6 |
| BS + BP + BL Group 2 | 12.5 ± 20.5 |

As shown in Table 12, in the attack test of *Vibrio parahaemolyticus* for the shrimp, BS+BP+BL Groups 1 and 2 provided with the feed compositions of Examples 5 and 6 including *Bacillus subtilis*, *Bacillus pumilus*, and *Bacillus licheniformis* showed a higher survival rate than Control Group 1, to which the feed composition of Comparative Example 1 was administered, and BS Groups 3 and 4, to which the feed compositions of Comparative Examples 3 and 4 were administered.

Experimental Example 4. Evaluation of Preventive Effect of Feed Composition on WSSV In order to confirm antiviral activity of the feed compositions including *Bacillus subtilis, Bacillus pumilus*, and *Bacillus licheniformis*, the attack test was carried out such that the shrimp were attacked by white spot syndrome virus. In the case of the white spot syndrome virus, viruses isolated from whiteleg shrimp (*Litopenaues vannamei*) infected with WSSV were obtained from domestic farms in 2017 and used for the test. The attack test was carried out as follows: the feed compositions of the Examples were given to shrimp for 6 weeks, and then the shrimp having the same weight (average weight: 6.25 g) were placed into 4 replicates with 96 shrimp per group. The inoculation concentration of the virus was $4.1 \times 10^5$ copies/µL, and each shrimp was inoculated intramuscularly with 100 µL of virus using a syringe. The final inoculation concentration per shrimp was $4.1 \times 10^7$ copes/µL.

After the inoculation, the mortality of shrimp and their swimming states were confirmed. The test feed was given three times a day (at 8:30, 13:30, and 18:30) in a divided dose in a restricted manner (10% to 12% of fish body weight), and the degree of mortality was observed for 125 hours. The results are shown in Table 13 below.

TABLE 13

| Treatment | Survival (%) Trial |
| --- | --- |
| Control Group 1 | 23.21 ± 3.57 |
| BS Group 4 | 25.00 ± 18.0 |
| BS + BP + BL Group 1 | 41.1 ± 17.9 |
| BS + BP + BL Group 2 | 28.57 ± 15.4 |

As shown in Table 13, in the attack test of white spot syndrome virus for the shrimp, BS+BP+BL Groups 1 and 2 provided with the feed compositions of Examples 5 and 6 including *Bacillus subtilis, Bacillus pumilus*, and *Bacillus licheniformis* showed a higher survival rate than Control Group 1, to which the feed composition of Comparative Example 1 was administered, and BS Group 4, to which the feed composition of Comparative Example and 4 was administered.

Experimental Example 5. Evaluation of Preventive Effect of Feed Composition on Coinfection of WSSV and AHPND In order to confirm antibacterial and antiviral activities of the feed compositions including *Bacillus subtilis, Bacillus pumilus*, and *Bacillus licheniformis*, the attack test was carried out such that the shrimp were attacked by *Vibrio parahaemolyticus* and white spot syndrome virus. In the case of the *Vibrio* strain, AHPND (EMS)-induced strains isolated from Vietnam in 2013 were used for the test. In the case of the white spot syndrome virus, viruses isolated from whiteleg shrimp (*Litopenaues vannamei*) infected with WSSV were obtained from domestic farms in 2017 and used for the test. The attack test was carried out as follows: the feed compositions of the Examples were given to shrimp for 6 weeks, and then the shrimp having the same weight (average weight: 4.52 g) were placed into 4 replicates with 96 shrimp per group. The inoculation concentration of the virus was $8.3 \times 10^3$ copies/µL, and each shrimp was inoculated intramuscularly with 50 µL of virus using a syringe. The final inoculation concentration per shrimp was $4.1 \times 10^4$ copies/µL. Two days after the virus inoculation, the shrimp were infected with the *Vibrio* strain.

The bacteria were cultured at 30° C. with 150 rpm for 24 hours using a TSB+ medium, and a suspension of *Vibrio parahaemolyticus* was immersed at a concentration of $1.3 \times 10^5$ CFU/mL per tank. After the immersion, the mortality of shrimp and their swimming states were confirmed every hour. The test feed was given three times a day (at 8:30, 13:30, and 18:30) in a divided dose in a restricted manner (10% to 12% of fish body weight), and the degree of mortality was observed for 7 days. The results are shown in Table 14 below.

TABLE 14

| Treatment | Survival (%) Trial |
| --- | --- |
| Control Group 1 | 51.8 ± 13.5 |
| BS Group 4 | 62.5 ± 14.7 |
| BS + BP + BL Group 1 | 62.5 ± 6.8 |
| BS + BP + BL Group 2 | 66.1 ± 28.8 |

As shown in Table 14, in the attack test of *Vibrio parahaemolyticus* and white spot syndrome virus for the shrimp, BS+BP+BL Groups 1 and 2 provided with the feed compositions of Examples 5 and 6 including *Bacillus subtilis, Bacillus pumilus*, and *Bacillus licheniformis* showed a higher survival rate than Control Group 1, to which the feed composition of Comparative Example 1 was administered, and BS Group 4, to which the feed composition of Comparative Example and 4 was administered.

Based on the Examples above, the feed compositions including *Bacillus subtilis, Bacillus pumilus*, and *Bacillus licheniformis* according to the present disclosure can increase the growth of whiteleg shrimp, feed efficiency, digestibility, quality of culture water, and nonspecific immunity. In addition, it is expected that the present disclosure enables the production of high-protein whiteleg shrimp and thus can increase the marketability of the shrimp.

DEPOSITION NOS

Depository Institution: Korean Culture Center of Microorganisms (International Depositary Authority)
Accession No.: KCCM11143P
Deposition Date: 20101214
Accession No.: KCCM11144P
Deposition Date: 20101214
Accession No.: KCCM11270P
Deposition Date: 20120322

The invention claimed is:

1. A feed composition or a feed additive for improving the non-specific immune response of a crustacean subject against acute hepatopancreatic necrosis disease (AHPND), the composition or the additive comprising, as active ingredients, $1 \times 10^4$ CFU to $1 \times 10^{11}$ CFU per gram of isolated *Bacillus* strains, wherein the *Bacillus* strains are *Bacillus subtilis* deposited as KCCM11143P, *Bacillus pumilus* deposited as KCCM11144P, and *Bacillus licheniformis* deposited as KCCM11270P.

2. The feed composition or the feed additive of claim 1, wherein the AHPND is caused by *Vibrio haemolyticus*.

3. The feed composition or the feed additive of claim 1, wherein the crustacean subject is a shrimp.

4. A feed composition or a feed additive for improving the non-specific immune response of a crustacean subject against white spot syndrome (WSS), the composition or the additive comprising, as active ingredients, 1×10⁴ CFU to 1×10¹¹ CFU per gram of isolated *Bacillus* strains, wherein the *Bacillus* strains are *Bacillus subtilis* deposited as KCCM11143P, *Bacillus pumilus* deposited as KCCM11144P, and *Bacillus licheniformis* deposited as KCCM11270P.

5. The feed composition or the feed additive of claim 4, wherein the WSS is caused by white spot syndrome virus (WSSV).

6. The feed composition or the feed additive of claim 4, wherein the crustacean subject is a shrimp.

7. A method of improving the non-specific immune response of a crustacean subject against acute hepatopancreatic necrosis disease (AHPND) comprising feeding the subject with an effective dose of the feed composition or the feed additive of claim 1.

8. The method of claim 7, wherein the crustacean subject is a shrimp.

9. A method of improving the non-specific immune response of a crustacean subject against white spot syndrome (WSS) comprising feeding the subject with an effective dose of the feed composition or the feed additive of claim 4.

10. The method of claim 9, wherein the crustacean subject is a shrimp.

* * * * *